United States Patent [19]

Ulrich

[11] Patent Number: 4,994,461
[45] Date of Patent: Feb. 19, 1991

[54] 1,4-DIHYDROPYRIDINE ENANTIOMERS

[75] Inventor: Wolf-Rüdiger Ulrich, Constance, Fed. Rep. of Germany

[73] Assignee: Byk Gulden Lomberg Chemische Fabrik GmbH, Constance, Fed. Rep. of Germany

[21] Appl. No.: 401,453

[22] PCT Filed: Mar. 24, 1988

[86] PCT No.: PCT/EP88/00239

§ 371 Date: Sep. 19, 1989

§ 102(e) Date: Sep. 19, 1989

[87] PCT Pub. No.: WO88/07525

PCT Pub. Date: Oct. 6, 1988

[30] Foreign Application Priority Data

Mar. 27, 1987 [CH] Switzerland .................. 01190/87
Mar. 27, 1987 [CH] Switzerland .................. 01184/87

[51] Int. Cl.$^5$ .................. A61K 31/495; A61K 31/44; C07D 401/12
[52] U.S. Cl. .................. 514/252; 514/253; 514/318; 544/360; 544/364; 546/193; 546/194
[58] Field of Search .................. 544/360, 364; 546/193, 546/194; 514/252, 253, 318

[56] References Cited

U.S. PATENT DOCUMENTS

| | | | |
|---|---|---|---|
| 4,031,104 | 6/1977 | Bossert et al. | 546/321 |
| 4,145,432 | 5/1979 | Sato et al. | 546/321 |
| 4,380,547 | 4/1983 | Materne et al. | 46/270 |
| 4,491,582 | 1/1985 | Loev et al. | 544/360 |
| 4,497,808 | 2/1985 | Zimmermanni et al. | 546/187 |
| 4,505,920 | 3/1985 | Loev et al. | 546/321 |
| 4,510,310 | 4/1985 | Wehinger et al. | 546/321 |
| 4,558,058 | 12/1985 | Schönafinger et al. | 546/277 |
| 4,603,135 | 7/1986 | Meguro et al. | 544/360 |
| 4,707,486 | 11/1987 | Flockerzi et al. | 546/194 |

OTHER PUBLICATIONS

Shibanuma et al. Chem. Pharm. Bull. 28(9) 2809-2812 (1980).
Wehinger et al, Chem Abst. 105-133753f (1986).
Tamazawa, J. Med. Chem., 29, 2504 to 2511, 1986.

Primary Examiner—Cecilia Shen
Attorney, Agent, or Firm—Berman, Aisenberg & Platt

[57] ABSTRACT

Enantiomerically-pure dihydropyridines of formula I

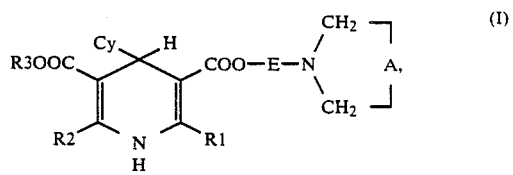

are effective vasodilators useful for treating coronary diseases. They have particularly advantageous properties with regard to extent and controllability of blood pressure lowering, a surprisingly small (and for repeated administration—vanishing) increase in heart rate, excellent bioavailability, high therapeutic index, lack of central side effects, lack of kinetic interactions with other substances, absence of tolerance development, well-balanced physical properties and high stability. A new process for preparing these compounds is also presented.

22 Claims, No Drawings

1,4-DIHYDROPYRIDINE ENANTIOMERS

FIELD OF APPLICATION OF THE INVENTION

The invention relates to novel enantiomers processes for their preparation, their use and medicaments which contain them. The compounds according to the invention are used in the pharmaceutical industry for the preparation of medicaments.

1. Known Prior Art

It is known that certain 1,4-dihydropyridine derivatives substituted in the 4-position have pharmacologically useful properties. It is also known that these 1,4-dihydropyridine derivatives, provided that they are differently (asymmetrically) substituted in positions 2 and 6 and/or in positions 3 and 5 - have a centre of chirality in position 4. It is also known that the pharmacological properties of the 1,4-dihydropyridines can be influenced by the absolute configuration in the 4-position. Because of these different pharmacological properties, various attempts have already been made to prepare pure 1,4-dihydropyridine enantiomers [see, for example, German Offenlegungsschrift 2,935,451, German Offenlegungsschrift 3,320,616, EP-A2 0166296, Shibaruma et al. Chem. Pharm. Bull. 28, 2809 (1980)]. However, either the known processes cannot be used to prepare all possible enantiomers of known 1,4-dihydropyridines or these processes give the pure 1,4-dihydropyridine enantiomers only in low yields or in insufficient purity.

2. Description of the Invention

Surprisingly, a novel process for the preparation of pure, optically active 1,4-dihydropyridine enantiomers has now been found, which gives the desired enantiomers in good yield and high purity. This process can be used for the preparation of novel enantiomers of the known 1,4-dihydropyridines.

The invention thus relates firstly to pure dihydropyridine enantiomers of the formula I

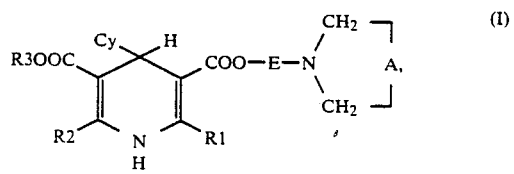

wherein Cy represents a cyclic radical of the formula

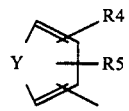

in which Y denotes oxygen (O), sulphur (S), vinylene (—CH=CH—), azomethine (—CH=N—) or a group of the formula

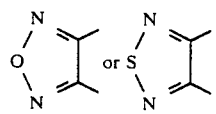

R1 and R2 are identical or different and denote hydrogen, 1–6C-alkyl or 3–7C-alkoxyalkyl, R3 denotes 1–6C-alkyl or 3–7C-alkoxyalkyl, R4 and R5 are identical or different and denote hydrogen, hydroxyl, halogen, nitro, cyano, trifluoromethyl, 1–4C-alkyl, 1–4C-alkoxy, completely or partially fluorine-substituted 1–4C-alkoxy, 1–4C-alkoxycarbonyl or 2–5C-acyl or together denote methylenedioxy, or denote amino or mono- or di-1–4C-alkylamino, E denotes straight-chain or branched 2–5C-alkylene which may be substituted by 1–4C-alkoxy or aryl, A denotes —CH$_2$—C(R6)R7—CH$_2$— or —CH$_2$—NR8—CH$_2$—, R6 denotes hydrogen (H) or aryl and R7 denotes aryl or arylcarbonyl, R8 denotes aryl, aryl-1–4C-alkyl, aryl-2–4C-alkenyl, aryl-2–4C-alkynyl, diaryl-1–4C-alkyl, heteroaryl, heteroaryl-1–4C-alkyl, heteroaryl-aryl-1–4C-alkyl, diheteroaryl-1–4C-alkyl, arylcarbonyl, heteroarylcarbonyl, arylsulphonyl, aryl-1–4C-alkylcarbonyl or aryl-2–4C-alkenylcarbonyl, aryl representing a ring of the formula

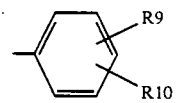

wherein R9 and R10 are identical or different and have the meaning of hydrogen (H), 1–4C-alkyl, 1–4C-alkoxy, halogen, hydroxyl or trifluoromethyl, and heteroaryl represents a 5-membered or 6-membered heterocylic radical having one heteroatom or two identical or different heteroatoms from the group consisting of oxygen (O), sulphur (S) or nitrogen (N), which is unsaturated or partially or completely saturated and which may carry one or two substituents from the group consisting of 1–4C-alkyl, 1–4C-alkoxy, halogen, trifluoromethyl or cyano, and the salts of these compounds, except for the (S)-enantiomer of the compound in which Cy has the meaning of 3-nitrophenyl, R1, R2 and R3 denote methyl, E denotes propylene, A represents CH$_2$—C(R6)R7—CH$_2$ and R6 and R7 denote phenyl.

1–6C-Alkyl is straight-chain or branched and denotes, for example, a hexyl, neopentyl, isopentyl, butyl, isobutyl, sec-butyl, tert-butyl, propyl, isopropyl or, in particular, ethyl or methyl radical.

3–7C-Alkoxyalkyl represents, for example, an ethoxyethyl, propoxyethyl, isopropoxyethyl, butoxyethyl, methoxypropyl, 2-methoxy-1-methylethyl, 2-ethoxy-1-methylethyl or, in particular, methoxyethyl radical.

According to the invention, halogen denotes bromine, fluorine and, in particular, chlorine.

1–4C-Alkyl is straight-chain or branched and means, for example, a butyl, isobutyl, sec-butyl, tert-butyl propyl, isopropyl, ethyl or, in particular methyl radical.

1–4C-Alkoxy contains, in addition to the oxygen atom, one of the above-mentioned 1–4C-alkyl radicals. The methoxy radical and the ethoxy radical are preferred.

1–4C-Alkoxy which is completely or partially substituted by fluorine is, for example, 1,1,2,2-tetrafluoroethoxy, trifluoromethoxy, 2,2,2-trifluoroethoxy, in particular, difluoromethoxy.

1–4C-Alkoxycarbonyl contains in addition to the carbonyl group, one of the above-mentioned 1–4C-alkoxy radicals. The methoxycarbonyl radical and the ethoxycarbonyl radical are preferred.

2–5C-Acyl contains in addition to the carbonyl group, one of the above-mentioned 1–4C-alkyl radicals. The acetyl radical is preferred.

Mono- or di-1–4C-alkylamino contains in addition to the nitrogen atom, one or two of the above-mentioned 1–4C-alkyl radicals. Di-1–4C-alkylamino is preferred, in particular dimethyl-, diethyl- or diisopropylamino.

Straight-chain or branched 2–5C-alkylene is, for example, tetramethylene, 1,2-dimethylethylene, 2,2-dimethylethylene, isopropylidene, 1-methylethylene, 2-ethylpropylene and in particular ethylene or propylene.

Aryl represents phenyl which is substituted by R9 and R10. The following radicals may be mentioned as examples of preferred aryl radicals: phenyl, 4-methoxyphenyl 4-chlorophenyl, 4-methylphenyl, 4-fluorophenyl, 3-fluorophenyl, 3-chlorophenyl, 2-chlorophenyl, 3-methoxyphenyl, 2-methoxyphenyl, 2-ethoxyphenyl, 2-methylphenyl 3-chloro-4-methylphenyl, 3,4-dichlorophenyl, 3,6-dichlorophenyl, 2,4-dimethylphenyl, 2,6-dimethylphenyl, 3,4-dimethylphenyl, 3,4-methylenedioxyphenyl, 2-trifluoromethylphenyl and 3-trifluoromethylphenyl.

Aryl-1–4C-alkyl represents one 1–4C-alkyl which is substituted by aryl. The following radicals may be mentioned as examples of preferred aryl-1–4C-alkyl radicals: 4-methylbenzyl, 4-methoxybenzyl, 4-chlorobenzyl, 1-phenylethyl, 2-phenylethyl, 3-chlorobenzyl, 2,5-dimethylbenzyl, 4-fluorobenzyl, 3-methylbenzyl and in particular benzyl.

Aryl-2–4C-alkenyl and aryl-2–4C-alkynyl represent alkenyl and alkynyl radicals having 2 to 4 carbon atoms, which are substituted by aryl. The 3-phenyl-2-propenyl radical and the 3-phenyl-2-propynyl radical may be mentioned as examples.

Arylcarbonyl represents a carbonyl group which is substituted by aryl. The 4-chlorophenylcarbonyl, 2-hydroxyphenylcarbonyl (salicyloyl), the 4-hydroxyphenylcarbonyl and in particular the 4-fluorophenylcarbonyl and the benzoyl group may be mentioned as examples of preferred arylcarbonyl groups.

The following radicals may be mentioned as examples of preferred (substituted) heteroaryl radicals: furyl, in particular 2-furyl, thienyl, in particular 2-thienyl, pyrimidyl, in particular 2-pyrimidyl, 3-cyano-2-pyridyl, thiazolyl, in particular 2-thiazolyl, and pyridyl, in particular 3-pyridyl and preferably 2-pyridyl.

Heteroarylcarbonyl represents a carbonyl group which is substituted by heteroaryl. The nicotinoyl radical and the 2-furoyl radical may be mentioned as examples of preferred heteroarylcarbonyl radicals.

Heteroaryl-1–4C-alkyl is 1–4C-alkyl which is substituted by heteroaryl. Heteroaryl-1–4C-alkyl is, for example, 2-(2-pyridyl)-ethyl.

Diaryl-1–4C-alkyl is 1–4C-alkyl which is substituted by two aryl radicals. Diaryl-1–4C-alkyl is, in particular diphenylmethyl (benzhydryl) or substituted benzhydryl, such as, for example, 4,4′-difluorobenzhydryl, 4,4′-dimethylbenzhydryl, 4,4′-dimethoxyhydryl or 4,4′-dichlorobenzhydryl.

Heteroaryl-aryl-1–4C-alkyl is 1–4C-alkyl which is substituted by heteroaryl and aryl. Diheteroaryl-aryl-1–4C-alkyl is, for example, 2-pyridylphenylmethyl.

Diheteroaryl-1–4C-alkyl is 1–4C-alkyl which is substituted by two heteroaryl radicals. Diheteroaryl-1–4C-alkyl is, for example, dipyrid-2-ylmethyl.

Arylsulphonyl represents a sulphonyl group which is substituted by aryl. The 4-chlorophenylsulphonyl radical and the 4-methoxyphenylsulphonyl radical may be mentioned as examples of preferred arylsulphonyl radicals.

The 2-phenylpropionyl radical may be mentioned as an example of an aryl-1–4C-alkylcarbonyl radical. The cinnamoyl radical may be mentioned as an example of an aryl-2–4C-alkenylcarbonyl radical.

Suitable salts are all salts with acids. The pharmacologically acceptable salts of the inorganic or organic acids usually used in the pharmaceutical industry may be mentioned in particular. Pharmacologically unacceptable salts, which may initially be obtained as products of the process, for example in the preparation of the compounds according to the invention on an industrial scale, are converted into pharmacologically acceptable salts by processes known to the skilled worker. Examples of suitable solvents of this type are water-soluble and water-insoluble acid addition salts, such as the hydrochloride, hydrobromide, hydriodide, phosphate, nitrate, sulphate, acetate, citrate gluconate, benzoate, hibenzate, fendizoate, butyrate, sulphosalicylate maleate, laurate, malate, fumarate, succinate, oxalate, tartrate, amsonate, metembonate, stearate, tosylate 2-hydroxy-3-naphtoate, 3-hydroxy-2-naphthoate or mesylate, as well as salts with bumetanide, furosemide, azosemide, galosemide, besunide, piretanide, etacrynic acid, tienilic acid or 4-chlorosulphamoylbenzoic acid.

The invention thus relates firstly to a novel pure 1,4-dihydropyridine enantiomer of the formula I which can be isolated or has been isolated for the first time.

The invention preferably relates to pure enantiomeric compounds of the formula I,
wherein
Cy denotes 3-nitrophenyl or 2,3-dichlorophenyl,
R1 and R2 are identical or different and denote 1–4C-alkyl,
R3 denotes 1–4C-alkyl,
E denotes ethylene or propylene.
A denotes —CH$_2$—C(R6)R7—CH$_2$— or —CH$_2$—NR8—CH—,
R6 denotes hydrogen (H) or phenyl,
R7 denotes phenyl and
R8 denotes aryl or benzhydryl, aryl representing a ring of the formula

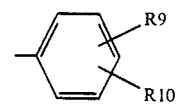

wherein R9 and R10 are identical or different and denote hydrogen (H), 1–4C-alkoxy or halogen,
and the salts of these compounds, except for the (S)-enantiomer of the compound in which Cy denotes 3-nitrophenyl, R1, R2 and R3 denote methyl, E denotes propylene, A represents CH$_2$—C(R6)-R7—CH$_2$ and R6 and R7 denote phenyl.

An embodiment (embodiment a) of the invention comprises pure enantiomeric compounds of the formula 1, wherein Cy, R1, R2, R3, R4, R5 and E have the meanings stated at the outset,
A denotes —CH$_2$—C(R6)R7—CH—,
R6 denotes hydrogen (H) and
R7 denotes aryl or arylcarbonyl aryl having the meaning stated at the outset, and the salts of these compounds.

The embodiment a can be characterised by the following formula Ia

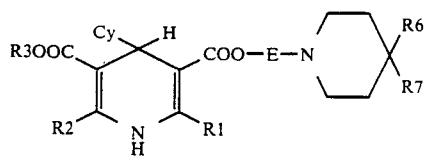

wherein the substituents and symbols have the meanings stated for embodiment a.

Compounds of embodiment a which are to be singled out are those of the formula Ia, wherein
- Cy denotes 3-nitrophenyl, 2-chlorophenyl, 2,3-dichlorophenyl, 2-trifluoromethylphenyl, 2-difluoromethoxyphenyl, 2,3-methylenedioxyphenyl or benzoxdiazolyl,
- R1 denotes methyl or ethyl,
- R2 denotes methyl or ethyl,
- R3 denotes methyl or ethyl,
- E denotes ethylene or propylene,
- R6 denotes hydrogen and
- R7 denotes phenyl, benzoyl, 4-chlorobenzoyl or 4-fluorobenzoyl, and their salts.

Particularly preferred compounds of embodiment a are those of the formula Ia, wherein
- Cy denotes 3-nitrophenyl,
- R1 denotes methyl,
- R2 denotes methyl,
- R3 denotes methyl,
- E denotes ethylene or propylene,
- R6 denotes hydrogen and
- R7 denotes phenyl, and their salts.

The following may be mentioned as examples of particularly noteworthy compounds of embodiment a:

3-methyl 5-[2-(4-phenylpiperid-1-yl)-ethyl] (+)-1,4-dihydro-2,6-dimethyl-4-(2-chlorophenyl)-pyridine-3,5-dicarboxylate, 3-methyl 5-[2-(4-phenylpiperid-1-yl)-ethyl] (+)-1,4-dihydro-2,6-dimethyl-4-(2,3-dichlorophenyl)-pyridine-3,5-dicarboxylate, 3-methyl 5-[2-(4-phenylpiperid-1-yl)-ethyl] (+)-1,4-dihydro-2,6-dimethyl-4-(2,1,3-benzoxdiazol-4-yl)-pyridine-3,5-dicarboxylate, 3-methyl 5-[3-(4-phenylpiperid-1-yl)-propyl] (+)-1,4-dihydro-2,6-dimethyl-4-(2-chlorophenyl)-pyridine-3,5-dicarboxylate, 3-methyl 5-[3-(4-phenylpiperid-1-yl)-propyl] (+)-1,4-dihydro-2,6-dimethyl-4-(2,3-dichlorophenyl)-pyridine-3,5-dicarboxylate, 3-methyl 5-[3-(4-phenylpiperid-1-yl)-propyl] (+)-1,4-dihydro-2,6-dimethyl-4-(2,1,3-benzoxdiazol-4-yl)-pyridine-3,5-dicarboxylate, 3-methyl 5-[2-(4-phenylpiperid-1-yl)-ethyl] (+)-1,4-dihydro-2,6-dimethyl-4-(3-nitrophenyl)-pyridine-3,5-dicarboxylate, 3-methyl 5-[3-(4-phenylpiperid-1-yl)-propyl] (+)-1,4-dihydro-2,6-dimethyl-4-(3-nitrophenyl)-pyridine-3,5-dicarboxylate, 3-methyl 5-{2-[4-(4-fluorobenzoyl)-piperid-1-yl]-ethyl} (+)-1,4-dihydro-2,6-dimethyl-4-(3-nitrophenyl)-pyridine-3,5-dicarboxylate, 3-methyl 5-{3-[4-(4-fluorobenzoyl)-piperid-1-yl]-propyl} (+)-1,4-dihydro-2,6-dimethyl-4-(3-nitrophenyl)-pyridine-3,5-dicarboxylate, 3-methyl 5-[2-(4-phenylpiperid-1-yl)-ethyl] (−)-1,4-dihydro-2,6-dimethyl-4-(2-chlorophenyl)-pyridine-3,5-dicarboxylate, 3-methyl 5-[2-(4-phenylpiperid-1-yl)-ethyl] (−)-1,4-dihydro-2,6-dimethyl-4-(2,3-dichlorophenyl)-pyridine-3,5-dicarboxylate, 3-methyl 5-[2-(4-phenylpiperid-1-yl)-ethyl] (−)-1,4-dihydro-2,6-dimethyl-4-(2,1,3-benzoxdiazol-4-yl)-pyridine-3,5-dicarboxylate, 3-methyl 5-[3-(4-phenylpiperid-1-yl)-propyl] (−)-1,4-dihydro-2,6-dimethyl-4-(2-chlorophenyl)-pyridine-3,5-dicarboxylate, 3-methyl 5-[3-(4-phenylpiperid-1-yl)-propyl] (−)-1,4-dihydro-2,6-dimethyl-4-(2,3-dichlorophenyl)-pyridine-3,5-dicarboxylate, 3-methyl 5-[3-(4-phenylpiperid-1-yl)-propyl] (−)-1,4-dihydro-2,6-dimethyl-4-(2,1,3-benzoxdiazol-4-yl)-pyridine-3,5-dicarboxylate, 3-methyl 5-[2-(4-phenylpiperid-1-yl)-ethyl] (−)-1,4-dihydro-2,6-dimethyl-4-(3-nitrophenyl)-pyridine-3,5-dicarboxylate, 3-methyl 5-[3-(4-phenylpiperid-1-yl)-propyl] (−)-1,4-dihydro-2,6-dimethyl-4-(3-nitrophenyl)-pyridine-3,5-dicarboxylate, 3-methyl 5-{2-[4-(4-fluorobenzoyl)-piperid-1-yl]-ethyl} (−)-1,4-dihydro-2,6-dimethyl-4-(3-nitrophenyl)-pyridine-3,5-dicarboxylate, 3-methyl 5-{3-[4-(4-fluorobenzoyl)-piperid-1-yl]-propyl} (−)-1,4-dihydro-2,6-dimethyl-4-(3-nitrophenyl)-pyridine-3,5-dicarboxylate, and their salts.

A further embodiment (embodiment b) of the invention comprises pure enantiomeric compounds of the formula I, wherein Cy, R1, R2, R3, R4, R5 and E have the meanings stated at the outset, A denotes —CH$_2$—NR8—CH$_2$—, R8 denotes aryl, aryl-1–4C-alkyl, aryl-2–4C-alkenyl, aryl-2–4C-alkynyl, diaryl-1–4C-alkyl, heteroaryl, heteroaryl-1–4C-alkyl, heteroaryl-aryl-1–4C-alkyl, diheteroaryl-1–4C-alkyl, arylcarbonyl, heteroarylcarbonyl, arylsulphonyl, aryl-1–4C-alkylcarbonyl or aryl-2–4C-alkenylcarbonyl, aryl and heteroaryl having the meanings stated at the outset, and the salts of these compounds.

Embodiment b can be characterised by the following formula Ib

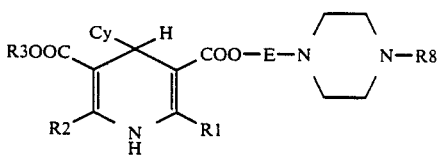

wherein the substituents and the symbols have the meanings stated for embodiment b.

Compounds of embodiment b which are to be singled out are those of the formula Ib, wherein
- Cy denotes 3-nitrophenyl, 2-chlorophenyl, 2,3-dichlorophenyl, 2-trifluoromethylphenyl, 2-difluoromethoxyphenyl, 2,3-methylenedioxyphenyl or benzoxdiazolyl,
- R1 denotes methyl or ethyl,
- R2 denotes methyl or ethyl,
- R3 denotes methyl or ethyl,
- E denotes ethylene or propylene and
- R8 denotes phenyl, 2-methoxyphenyl, 2-ethoxyphenyl, 2-ethoxy-4-fluorophenyl, 3-trifluoromethylphenyl, 3-methoxyphenyl, 3,4-methylenedioxyphenyl, 2-methylphenyl, 2,4-dimethylphenyl, 2,6- dimethylphenyl, 2-pyridyl or benzhydryl, and their salts.

Particularly preferred compounds of embodiment b are those of the formula Ib, wherein
Cy denotes 3-nitrophenyl,
R1 denotes methyl,
R2 denotes methyl,
R3 denotes methyl,
E denotes ethylene or propylene and
R8 denotes phenyl, 2-methoxyphenyl, 2-ethoxyphenyl, 2-ethoxy-4-fluorophenyl or benzhydryl,
and their salts.

The following may be mentioned as examples of particularly noteworthy compounds of embodiment b:

3-methyl 5-{2-[4-(2-methoxyphenyl)-1-piperazinyl]-ethyl} (+)-1,4-dihydro-2,6-dimethyl-4-(2-chlorophenyl)-pyridine-3,5-dicarboxylate, 3-methyl 5-{2-[4-(2-methoxyphenyl)-1-piperazinyl]-ethyl} (+)-1,4-dihydro-2,6-dimethyl-4-(2,3-dichlorophenyl)-pyridine-3,5-dicarboxylate, 3-methyl 5-{2-[4-(2-methoxyphenyl)-1-piperazinyl]-ethyl} (+)-1,4-dihydro-2,6-dimethyl-4-(2,1,3-benzoxdiazol-4-yl)-pyridine-3,5-dicarboxylate, 3-methyl 5-{3-[4-(2-methoxyphenyl)-1-piperazinyl]-propyl} (+)-1,4-dihydro-2,6-dimethyl-4-(2-chlorophenyl)-pyridine-3,5-dicarboxylate, 3-methyl 5-(3-[4-(2-methoxyphenyl)-1-piperazinyl]-propyl} (+)-1,4-dihydro-2,6-dimethyl-4-(2,3-dichlorophenyl)-pyridine-3,5-dicarboxylate, 3-methyl 5-{3-[4-(2-methoxyphenyl)-1-piperazinyl]-propyl} (+)-1,4-dihydro-2,6-dimethyl-4-(2,1,3-benzoxdiazol-4-yl)-pyridine-3,5-dicarboxylate, 3-methyl 5-[2-(4-benzhydryl-1-piperazinyl)-ethyl] (+)-1,4-dihydro-2,6-dimethyl-4-(2-chlorophenyl)-pyridine-3,5-dicarboxylate, 3-methyl 5-[2-(4-benzhydryl-1-piperazinyl)-ethyl] (+)-1,4-dihydro-2,6-dimethyl-4-(2,3-dichlorophenyl)-pyridine-3,5-dicarboxylate, 3-methyl 5-[2-(4-benzhydryl-1-piperazinyl)-ethyl] (+)-1,4-dihydro-2,6-dimethyl-4-(2,1,3-benzoxdiazol-4-yl)-pyridine-3,5-dicarboxylate, 3-methyl 5-[3-(4-benzhydryl-1-piperazinyl)-propyl] (+)-1,4-dihydro-2,6-dimethyl-4-(2-chlorophenyl)-pyridine-3,5-dicarboxylate, 3-methyl 5-[3-(4-benzhydryl-1-piperazinyl)-propyl] (+)-1,4-dihydro-2,6-dimethyl-4-(2,3-dichlorophenyl)-pyridine-3,5-dicarboxylate, 3-methyl 5-[3-(4-benzhydryl-1-piperazinyl)-propyl] (+)-1,4-dihydro-2,6-dimethyl-4-(2,1,3-benzoxdiazol-4-yl)-pyridine-3,5-dicarboxylate, 3-methyl 5-{2-[4-(2-methoxyphenyl)-1-piperazinyl]-ethyl} (+)-1,4-dihydro-2,6-dimethyl-4-(3-nitrophenyl)-pyridine-3,5-dicarboxylate, 3-methyl 5-{3-[4-(2-methoxyphenyl)-1-piperazinyl]-propyl} (+)-1,4-dihydro-2,6-dimethyl-4-(3-nitrophenyl)-pyridine-3,5-dicarboxylate, 3-methyl 5-[2-(4-phenyl-1-piperazinyl)-ethyl] (+)-1,4-dihydro-2,6-dimethyl-4-(3-nitrophenyl)-pyridine-3,5-dicarboxylate, 3-methyl 5-[3-(4-phenyl-1-piperazinyl)-propyl] (+)-1,4-dihydro-2,6-dimethyl-4-(3-nitrophenyl)-pyridine-3,5-dicarboxylate, 3-methyl 5-(2-[4-(2-pyridyl)-1-piperazinyl]-ethyl} (+)-1,4-dihydro-2,6-dimethyl-4-(3-nitrophenyl)-pyridine-3,5-dicarboxylate, 3-methyl 5-{3-[4-(2-pyridyl)-1-piperazinyl]-propyl} (+)-1,4-dihydro-2,6-dimethyl-4-(3-nitrophenyl)-pyridine-3,5-dicarboxylate, 3-methyl5-[2-(4-benzhydryl)-1-piperazinyl]-ethyl (+)-1,4-dihydro-2,6-dimethyl-4-(3-nitrophenyl)-pyridine-3,5-dicarboxylate, 3-methyl 5-[3-(4-benzhydryl)-1-piperazinyl]-propyl(+)-1,4-dihydro-2,6-dimethyl-4-(3-nitrophenyl)-pyridine-3,5-dicarboxylate, 3-methyl 5-{3-[4-(2-ethoxyphenyl)-1-piperazinyl]-propyl} (+)-1,4-dihydro-2,6-dimethyl-4-(3-nitrophenyl)-pyridine-3,5-dicarboxylate, 3-methyl 5-{2-[4-(2-ethoxyphenyl)-1-piperazinyl]-ethyl} (+)-1,4-dihydro-2,6-dimethyl-4-(3-nitrophenyl)-pyridine-3,5-dicarboxylate, 3-methyl 5-{3-[4-(3-trifluoromethylphenyl)-1-piperazinyl]-propyl} (+)-1,4-dihydro-2,6-dimethyl-4-(3-nitrophenyl)-pyridine-3,5-dicarboxylate, 3-methyl 5-{2-[4-(3-trifluoromethylphenyl)-1-piperazinyl]-ethyl} (+)-1,4-dihydro-2,6-dimethyl-4-(3-nitrophenyl)-pyridine-3,5-dicarboxylate, 3-methyl 5-{3-[4-(3-methoxyphenyl)-1-piperazinyl]-propyl} (+)-1,4-dihydro-2,6-dimethyl-4-(3-nitrophenyl)-pyridine-3,5-dicarboxylate, 3-methyl 5-{2-[4-(3-methoxyphenyl)-1-piperazinyl]-ethyl} (+)-1,4-dihydro-2,6-dimethyl-4-(3-nitrophenyl)-pyridine-3,5-dicarboxylate, 3-methyl 5-{3-[4-(3,4-methylenedixoyphenyl)-1-piperazinyl]-propyl} (+)-1,4-dihydro-2,6-dimethyl-4-(3-nitrophenyl)-pyridine-3,5-dicarboxylate, 3-methyl 5-{2-[4-(3,4-methylenedixoyphenyl)-1-piperazinyl]-ethyl} (+)-1,4-dihydro-2,6-dimethyl-4-(3-nitrophenyl)-pyridine-3,5-dicarboxylate, 3-methyl 5-{3-[4-(2-tolyl)-1-piperazinyl]-propyl} (+)-1,4-dihydro-2,6-dimethyl-4-(3-nitrophenyl)-pyridine-3,5-dicarboxylate, 3-methyl 5-{2-[4-(2-tolyl)-1-piperazinyl]-ethyl} (+)-1,4-dihydro-2,6-dimethyl-4-(3-nitrophenyl)-pyridine-3,5-dicarboxylate, 3-methyl 5-{3-[4-(2,4-dimethylphenyl)-1-piperazinyl]-propyl} (+)-1,4-dihydro-2,6-dimethyl-4-(3-nitrophenyl)-pyridine-3,5-dicarboxylate, 3-methyl5-{2-[4-(2,4-dimethylphenyl)-1-piperazinyl]-ethyl}(+)-1,4-dihydro-2,6-dimethyl-4-(3-nitrophenyl)-pyridine-3,5-dicarboxylate, 3-methyl 5-(3-[4-(2,6-dimethylphenyl)-1-piperazinyl]-propyl} (+)-1,4-dihydro-2,6-dimethyl-4-(3-nitrophenyl)-pyridine-3,5-dicarboxylate, 3-methyl 5-{2-[4-(2,6-dimethylphenyl)-1-piperazinyl]-ethyl}(+)-1,4-dihydro-2,6-dimethyl-4-(3-nitrophenyl)-pyridine-3,5-dicarboxylate, 3-methyl 5-{2-[4-(2-methoxyphenyl)-1-piperazinyl]-ethyl} (−)-1,4-dihydro-2,6-dimethyl-4-(2-chlorophenyl)-pyridine-3,5-dicarboxylate, 3-methyl 5-{2-[4-(2-methoxyphenyl)-1-piperazinyl]-ethyl} (−)-1,4-dihydro-2,6-dimethyl-4-(2,3-chlorophenyl)-pyridine-3,5-dicarboxylate, 3-methyl 5-{2-[4-(2-methoxyphenyl)-1-piperazinyl]-ethyl} (−)-1,4-dihydro-2,6-dimethyl-4-(2,1,3-benzoxdiazol-4-yl)-pyridine-3,5-dicarboxylate, 3-methyl 5-{3-[4-(2-methoxyphenyl)-1-piperazinyl]-propyl} (−)-1,4-dihydro-2,6-dimethyl-4-(2-chlorophenyl)-pyridine-3,5-dicarboxylate, 3-methyl 5-{3-[4-(2-methoxyphenyl)-1-piperazinyl]-propyl} (−)-1,4-dihydro-2,6-dimethyl-4-(2,3-dichlorophenyl)-pyridine-3,5-dicarboxylate, 3-methyl 5-{3-[4-(2-methoxyphenyl)-1-piperazinyl]-propyl} (−)-1,4-dihydro-2,6-dimethyl-4-(2,1,3-benzoxdiazol-4-yl)-pyridine-3,5-dicarboxylate, 3-methyl 5-[2-(4-benzhydryl-1-piperazinyl)-ethyl] (−)-1,4-dihydro-2,6-dimethyl-4-(2-chlorophenyl)-pyridine-3,5-dicarboxylate, 3-methyl 5-[2-(4-benzhydryl-1-piperazinyl)-ethyl] (−)-1,4-dihydro-2,6-dimethyl-4-(2,3-dichlorophenyl)-pyridine-3,5-dicarboxylate, 3-methyl 5-[2-(4-benzhydryl-1-piperazinyl)-ethyl] (−)-1,4-dihydro-2,6-dimethyl-4-(2,1,3-benzoxdiazol-4-yl)-pyridine-3,5-dicarboxylate, 3-methyl 5-[3-(4-benzhydryl-1-piperazinyl)-propyl](−)-1,4-dihydro-2,6-dimethyl-4-(2-chlorophenyl)-pyridine-3,5-dicarboxylate, 3-methyl 5-[3-(4-benzhydryl-1-piperazinyl)-propyl] (−)-1,4-dihydro-2,6-dimethyl-4-(2,3-dichlorophenyl)-pyridine-3,5-dicarboxylate, 3-methyl 5-[3-(4-benzhydryl-1-piperazinyl)-propyl](−)-1,4-dihydro-2,6-dimethyl-4-(2,1,3-benzoxdiazol-4-yl)-pyridine-3,5-dicarboxylate, 3-methyl 5-{2-[4-(2-methoxyphenyl)-1-piperazinyl]-ethyl} (−)-1,4-dihydro-2,6-dimethyl-4-(3-nitrophenyl)-pyridine-3,5-dicarboxylate, 3-methyl 5-{3-[4-(2-methoxyphenyl)-1-piperazinyl]-propyl} (−)-1,4-dihydro-2,6-dimethyl-4-(3-nitrophenyl)-pyridine-3,5-dicarboxylate, 3-methyl 5-[2-(4-phenyl-1-piperazinyl)-ethyl] (−)-1,4-dihydro-2,6-dimethyl-4-(3-nitrophenyl)-pyridine-3,5-dicarboxylate, 3-methyl 5-[3-(4-phenyl-1-piperazinyl)-propyl] (−)-1,4-dihydro-2,6-dimethyl-4-(3-nitrophenyl)-pyridine-3,5-dicarboxylate, 3-methyl 5-{2-[4-(2-pyridyl)-1-piperazinyl]-ethyl} (−)-1,4-dihydro-2,6-dimethyl-4-(3-nitrophenyl)-pyridine-3,5-dicarboxylate, 3-methyl 5-{3-[4-(2-pyridyl)-1-piperazinyl]-propyl} (−)-1,4-dihydro-2,6-dimethyl-4-(3-nitrophenyl)-pyridine-3,5-dicarboxylate, 3-methyl 5-[2-(4-benzhydryl)-1-piperazinyl]-ethyl (−)-1,4-dihydro-2,6-dimethyl-4-(3-nitrophenyl)-pyridine-3,5-dicarboxylate, 3-methyl 5-[3-(4-benzhydryl)-1-piperazinyl]-propyl(−)-1,4-dihydro-2,6-dimethyl-4-(3-nitrophenyl)-pyridine-3,5-dicarboxylate, 3-methyl 5-{3-[4-(2-ethoxyphenyl)-1-piperazinyl]-propyl} (−)-1,4-dihydro-2,6-dimethyl-4-(3-nitrophenyl)-pyridine-3,5-dicarboxylate, 3-methyl 5-{3-[4-(3-ethoxyphenyl)-1-piperazinyl]-ethyl} (−)-1,4-dihydro-2,6-dimethyl-4-(3-nitrophenyl)-pyridine-3,5-dicarboxylate, 3-methyl 5-{3-[4-(3-trifluoromethylphenyl)-1-piperazinyl]-propyl} (−)-1,4-dihydro-2,6-dimethyl-4-(3-nitrophenyl)-pyridine-3,5-dicarboxylate, 3-methyl 5-{2-[4-(3-trifluoromethylphenyl)-1-piperazinyl]-ethyl} (−)-1,4-dihydro-2,6-dimethyl-4-(3-nitrophenyl)-pyridine-3,5-dicarboxylate, 3-methyl 5-{3-[4-(3-methoxyphenyl)-1-piperazinyl]-propyl} (−)-1,4-dihydro-2,6-dimethyl-4-(3-nitrophenyl)-pyridine-3,5-dicarboxylate, 3-methyl 5-{2-[4-(3-methoxyphenyl)-1-piperazinyl]-ethyl} (−)-1,4-dihydro-2,6-dimethyl-4-(3-nitrophenyl)-pyridine-3,5-dicarboxylate, 3-methyl 5-{3-[4-(3,4-methylenedixoyphenyl)-1-piperazinyl]-propyl} (−)-1,4-dihydro-2,6-dimethyl-4-(3-nitrophenyl)-pyridine-3,5-dicarboxylate, 3-methyl 5-(2-[4-(3,4-methylenedioxyphenyl)-1-piperazinyl]-ethyl} (−)-1,4-dihydro-2,6-dimethyl-4-(3-nitrophenyl)-pyridine-3,5-dicarboxylate, 3-methyl 5-{3-[4-(2-tolyl)-1-piperazinyl]-propyl} (−)-1,4-dihydro-2,6-dimethyl-4-(3-nitrophenyl)-pyridine-3,5-dicarboxylate, 3-methyl 5-{2-[4-(2-tolyl)-1-piperazinyl]-ethyl} (−)-1,4-dihydro-2,6-dimethyl-4-(3-nitrophenyl)-pyridine-3,5-dicarboxylate, 3-methyl 5-{3-[4-(2,4-dimethylphenyl)-1-piperazinyl]-propyl} (−)-1,4-dihydro-2,6-dimethyl-4-(3-nitrophenyl)-pyridine-3,5-dicarboxylate, 3-methyl 5-{2-[4-(2,4-dimethylphenyl)-1-piperazinyl]-ethyl} (−)-1,4-dihydro-2,6-dimethyl-4-(3-nitrophenyl)-pyridine-3,5-dicarboxylate, 3-methyl 5-{3-[4-(2,6-dimethylphenyl)-1-piperazinyl]-propyl} (−)-1,4-dihydro-2,6-dimethyl-4-(3-nitrophenyl)-pyridine-3,5-dicarboxylate, 3-methyl 5-{2-[4-(2,6-dimethylphenyl)-1-piperazinyl]-ethyl} (−)-1,4-dihydro-2,6-dimethyl-4-(3-nitrophenyl)-pyridine-3,5-dicarboxylate, and their salts.

A further embodiment (embodiment c) of the invention comprises pure enantiomeric compounds of the formula I, wherein Cy, R1, R2, R3, R4, R5 and E have the meanings stated at the outset, A denotes —CH2—C(R6)-R7—CH—, R6 denotes aryl and R7 denotes aryl, aryl having the meaning stated at the outset, and the salts of these compounds, except for the (S)-enantiomer of the compound in which Cy denotes 3-nitrophenyl, R1, R2 and R3 denote methyl, E denotes propylene and R6 and R7 denote phenyl.

Embodiment c can be characterised by the following formula Ic

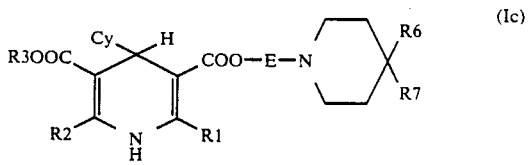

wherein the substituents and symbols have the meanings stated for embodiment c.

Compounds of embodiment c to be singled out are those of the formula Ic, wherein Cy denotes 3-nitrophenyl, 2-chlorophenyl, 2,3-dichlorophenyl, 2-trifluoromethylphenyl, 2-difluoromethoxyphenyl, 2,3-methylenedioxyphenyl or benzoxdiazolyl, R1 denotes methyl or ethyl,
R2 denotes methyl or ethyl,
R3 denotes methyl or ethyl,
E denotes ethylene or propylene,
R6 denotes phenyl or 4-methoxyphenyl and
R7 denotes phenyl or 4-methoxyphenyl,
and their salts, except for the (S)-enantiomer of the compound in which Cy denotes 3-nitrophenyl, R1, R2 and R3 denote methyl, E denotes propylene and R6 and R7 denote phenyl.

Particularly preferred compounds of embodiment c are those of the formula Ic, wherein Cy denotes 3-nitrophenyl or 2,3-dichlorophenyl,
R1 denotes methyl,
R2 denotes methyl,
R3 denotes methyl or ethyl,
E denotes ethylene or propylene,
R6 denotes phenyl and R7 denotes phenyl, and their salts, except for the (S)-enantiomer of the compound in which Cy denotes 3-nitrophenyl, R1, R2 and R3 denote methyl, E denotes propylene and R6 and R7 denote phenyl.

The following may be mentioned as examples of particularly noteworthy compounds of embodiment c:

3-methyl 5-{2-[4,4-di-(4-methoxyphenyl)-piperid-1-yl]-ethyl} (+)-1,4-dihydro-2,6-dimethyl-4-(3-nitrophenyl)-pyridine-3,5-dicarboxylate, 3-methyl 5-{3-[4,4-di-(4-methoxyphenyl)-piperid-1-yl]-propyl} (+)-1,4-dihydro-2,6-dimethyl-4-(3-nitrophenyl)-pyridine-3,5-dicarboxylate, 3-methyl 5-2-(4,4-diphenylpiperid-1-yl)-ethyl] (+)-1,4-dihydro-2,6-dimethyl-4-(2-chlorophenyl)-pyridine-3,5-dicarboxylate, 3-methyl 5-[2-(4,4-diphenylpiperid-1-yl)-ethyl] (+)-1,4-dihydro-2,6-dimethyl-4-(2,3-dichlorophenyl)-pyridine-3,5-dicarboxylate, 3-methyl 5-[2-(4,4-diphenylpiperid-1-yl)-ethyl] (+)-1,4-dihydro-2,6-dimethyl-4-(2,1,3-benzoxdiazol-4-yl)-pyridine-3,5-dicarboxylate, 3-methyl 5-[3-(4,4-diphenylpiperid-1-yl)-propyl] (+)-1,4-dihydro-2,6-dimethyl-4-(2-chlorophenyl)-pyridine-3,5-dicarboxylate, 3-methyl 5-[3-(4,4-diphenylpiperid-1-yl)-propyl] (+)-1,4-dihydro-2,6-dimethyl-4-(2,3-dichlorophenyl)-pyridine-3,5-dicarboxylate, 3-methyl 5-[3-(4,4-diphenylpiperid-1-yl)-propyl] (+)-1,4-dihydro-2,6-dimethyl-4-(2,1,3-benzoxdiazol-4-yl)-pyridine-3,5-dicarboxylate, 3-methyl5-[2-(4,4-diphenylpiperid-1-yl)-ethyl] (+)-1,4-dihydro-2,6-dimethyl-4-(3-nitrophenyl)-pyridine-3,5-dicarboxylate, 3-methyl 5-{2-[4,4-di-(4-methoxyphenyl)-piperid-1-yl]-ethyl} (−)-1,4-dihydro-2,6-dimethyl-4-(3-nitrophenyl)-pyridine-3,5-dicarboxylate, 3-methyl 5-{3-[4,4-di-(4-methoxyphenyl)-piperid-1-yl]-propyl} (−)-1,4-dihydro-2,6-dimethyl-4-(3 nitrophenyl)-pyridine-3,5-dicarboxylate, 3-methyl 5-[2-(4,4-diphenylpiperid-1-yl)-ethyl](−)-1,4-dihydro-2,6-dimethyl-4-(2-chlorophenyl)-pyridine-3,5-dicarboxylate, 3-methyl 5-[2-(4,4-diphenylpiperid-1-yl)-ethyl] (−)-1,4-dihydro-2,6-dimethyl-4-(2,3-dichlorophenyl)-pyridine-3,5-dicarboxylate, 3-methyl 5-[2-(4,4-diphenylpiperid-1-yl)-ethyl](−)-1,4-dihydro-2,6-dimethyl-4-(2,1,3-benzoxdiazol-4-yl)-pyridine-3,5-dicarboxylate, 3-methyl 5-[3-(4,4-diphenylpiperid-1-yl)-propyl] (−)-1,4-dihydro-2,6-dimethyl-4-(2-chlorophenyl)-pyridine-3,5-dicarboxylate, 3-methyl 5-[3-(4,4-diphenylpiperid-1-yl)-propyl] (−)-1,4-dihydro-2,6-dimethyl-4-(2.3-dichlorophenyl)-pyridine-3,5-dicarboxylate, 3-methyl 5-[3-(4,4-diphenylpiperid-1-yl)-propyl] (−)-1,4-dihydro-2,6-dimethyl-4-(2,1,3-benzoxdiazol-4-yl)-pyridine-3,5-dicarboxylate, 3-methyl 5-[3-(4,4-diphenyl-1-piperidinyl)-propyl](−)-1,4-dihydro-2,6-dimethyl-4-(3-nitrophenyl)-pyridine-3,5-dicarboxylate, and their salts.

Of particular interest, and therefore a preferred subject of the invention, are the enantiomers which, in the 4-position of the dihydropyridine, have the same configuration as the (−)-1-ethoxymethyl-1,4-dihydro-5-methoxycarbonyl-2,6-dimethyl-4-(3-nitrophenyl)-pyridine-3-carboxylic acid cinchonidine salt which can be used as a precursor and which rotates linearly polarised light of wavelength 589 nm through $[\alpha]^{22}_D = -63.4°$ (c=1, chloroform).

The invention furthermore relates to a process for the preparation of the compounds of the formula I

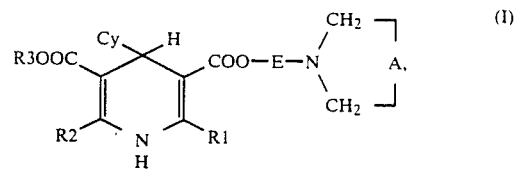

wherein Cy represents a cyclic radical of the formula

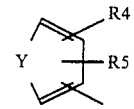

in which Y denotes oxygen (O), sulphur (S), vinylene (—CH=CH—), azomethine or a group of the formula

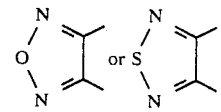

R1 and R2 are identical or different and denote hydrogen, 1–6C-alkyl or 3–7C-alkoxyalkyl, R3 denotes 1–6C-alkyl or 3–7C-alkoxyalkyl, R4 and R5 are identical or different and denote hydrogen, hydroxyl, halogen, nitro, cyano, trifluoromethyl, 1–4C-alkyl, 1–4C-alkoxy, completely or partially fluorine-substituted 1–4C-alkoxy, 1–4C-alkoxycarbonyl, 2–5C-acyl, together methylenedioxy, amino or mono or di-1–4C-alkylamino, E denotes straight-chain or branched 2–5C-alkylene which can be substituted by 1–4C-alkoxy or aryl, A denotes —CH2—C(R6)R7—CH2— or —CH2—NR8—CH2—, R6 denotes hydrogen (H) or aryl and R7 denotes aryl or arylcarbonyl, R8 denotes aryl, aryl-1–4C-alkyl, aryl-2–4C-alkenyl, aryl-2–4C-alkynyl, diaryl-1–4C-alkyl, heteroaryl, heteroaryl-1–4C-alkyl, heteroaryl-aryl-1–4C-alkyl, diheteroaryl-1–4C-alkyl, arylcarbonyl, heteroarylcarbonyl, arylsulphonyl, aryl-1–4C-alkylcarbonyl or aryl-2 4C-alkenylcarbonyl, aryl representing a ring of the formula

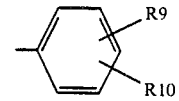

wherein R9 and R10 are identical or different and denote hydrogen (H), 1–4C-alkyl, 1–4C-alkoxy, halogen, hydroxyl or trifluoromethyl, and heteroaryl represents a 5-membered or 6-membered heterocyclic radical having one or two identical or different heteroatoms from the group consisting of oxygen (O), sulphur (S) or nitrogen (N), which heterocyclic radical is unsaturated or partially or completely saturated and which may carry one or two substituents from the group consisting of 1-4C-alkyl, 1-4C-alkoxy, halogen, trifluoromethyl and cyano, and their salts.

The process is characterised in that pure enantiomeric dihydropyridinecarboxylic acids which are protected at N and are of the formula II

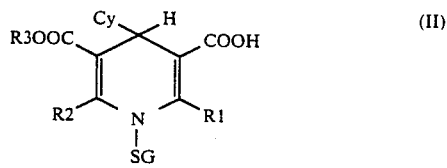

wherein R1, R2, R3 and Cy have the above-mentioned meanings and SG represents a protective group, are reacted with an omega-dihaloalkane Hal-E-Hal, wherein Hal denotes halogen and E has the above-mentioned meaning, and, after elimination of the protective group SG, the resulting haloalkyl ester III

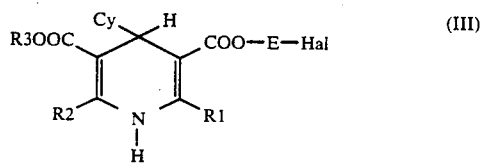

is reacted with an amine of the formula IV or a salt thereof

to give the end product I, and, if desired, salts of the compound I which are subsequently obtained are converted into the free bases or the compounds I are converted into their salts. The reaction of II with omega-dihaloalkanes is preferably carried out under basic conditions in the presence of a phase-transfer catalyst.

1,2-Dihaloethanes and 1,3-dihalopropanes, in particular 1,2-dibromomethane and 1,3-dibromopropane, may be mentioned as preferred omega-dihaloalkanes.

In addition to onium salts, such as, for example, tetrabutylammonium bromide or benzyltriethylammonium bromide, in particular crown ethers, such as dibenzo-[18]crown-6, dicyclohexyl-[18]-crown-6 and in particular [18]-crown-6, may be mentioned as phase transfer catalysts.

The bases used, which are employed at least in a molar ratio, preferably in excess, are inorganic bases, such as alkali metal hydroxides (for example sodium hydroxide or potassium hydroxide) or in particular alkali metal carbonates (for example sodium carbonate or preferably potassium carbonate). When the reaction is carried out in an anhydrous solvent, the hydroxides or carbonates used are preferably employed in finely pulverulent form.

The reaction is carried out (depending on the type of phase transfer catalyst and the base used) in water-containing or anhydrous organic solvents, or in a mixture of water and an organic solvent which is immiscible or scarcely miscible with water. The mixtures of water with chloroform, dichloromethane or benzene may be mentioned as examples of water/solvent mixtures. Dichloromethane, acetonitrile and acetone may be mentioned as examples of water-containing or anhydrous solvents.

The solvents, bases and phase transfer catalysts mentioned in the Examples are only an illustrative selection. From his technical knowledge, the skilled worker is familiar with further suitable combinations of solvents, bases and phase transfer catalysts.

The choice of reaction temperature in the reaction II with dihaloalkanes depends on the remaining reaction conditions, as a rule temperatures between 20° C. and the boiling point of the solvent used being preferred.

Particularly suitable protective groups are those groups which can be introduced readily, and in high yields, into the precursor from which the compound II is derived, which do not undergo any side reactions during the reaction of II with dihaloalkanes and which can be eliminated again readily at the end. Alkoxymethyl groups or benzyloxymethyl groups, in particular the ethoxymethyl group, may be mentioned as examples of preferred protective groups SG. Elimination of the protective group is carried out in an acidic medium, for example in 1 N hydrochloric acid or, preferably, in anhydrous formic acid, under reaction conditions familiar to the skilled worker. According to the invention, the protective group can also be eliminated after the reaction with the amine IV.

The reaction of the haloalkyl esters 111 with amines IV is carried out in a manner familiar to the skilled worker for the reaction of alkyl halides and secondary amines.

The reaction is carried out in suitable preferably inert organic solvents in the presence of water or without water. Examples which may be mentioned are ethers, such as dioxane, diethyl ether, tetrahydrofuran, glycol monoethyl ether or glycol dimethyl ether; ketones, such as acetone or ethyl methyl ketone aromatic hydrocarbons, such as xylene or toluene; or chlorinated hydrocarbons, such as methylene chloride chloroform, tetrachloroethylene or dichloroethane; or polar aprotic solvents such as dimethylformamide or dimethyl sulfoxide.

The reaction temperatures can be varied within a wide range, depending on the reactivity of educts. In general, the reaction is carried out at temperatures between 20° C. and 150° C., preferably between 20° C. and 100° C., in particular at the boiling point of the solvent used.

The process can be carried out under atmospheric pressure or under elevated pressure, the procedure under atmospheric pressure being the usual one. The reaction is carried out in the presence of a base (for example an inorganic carbonate, such as potassium carbonate) or with the use of an excess of amine IV.

The resulting compounds I according to the invention are isolated and purified in a manner known per se, for example by distilling off the solvent in vacuo and recrystallising the resulting residue from a suitable solvent or subjecting it to one of the conventional purification methods, such as, for example, column chromatography over a suitable carrier. Acid addition salts are obtained by dissolving the free base in a suitable solvent, for example in a chlorinated hydrocarbon, such as methylene chloride or chloroform, or a low molecular weight aliphatic alcohol (ethanol or isopropanol) or an open-chain or cyclic ether, such as dioxane or tetrahydrofuran, which contains the desired acid, or to which the desired acid is subsequently added.

The salts are isolated by filtration, reprecipitation, precipitation with a nonsolvent for the addition salt or by evaporation of the solvent.

Salts obtained can be converted into the free bases by adding an alkali, for example aqueous ammonia solution, and the said bases can in turn be converted into acid addition salts. In this way, pharmacologically unacceptable acid addition salts can be converted into pharmacologically acceptable acid addition salts.

Embodiments of the process are those in which the substituents and symbols have the meanings stated for the compounds of embodiments a, b and c. Processes to be singled out and preferred and particularly preferred processes are those in which the substituents and symbols have the meanings stated for the compounds to be singled out and preferred and particularly preferred compounds.

Of particular importance in this context is the use of the process according to the invention for the preparation of that enantiomer of 3-methyl-5-[3-(4,4-diphenyl-piperid-1-yl)-propyl] 1,4-dihydro-2,6-dimethyl-4-(3-nitrophenyl)-pyridine-3,5-dicarboxylate which rotates linearly polarised light of wavelength 589 nm in the (+) direction, that is to say of 3-methyl 5-[3-(4,4-diphenyl-piperid-1-yl)-propyl] (+)-1,4-dihydro-2,6-dimethyl-4-(3-nitrophenyl)-pyridine-3,5-dicarboxylate, and its salts, and of the corresponding (−)-enantiomer and its salts.

Without taking into account the absolute configuration in the 4-position of the 1,4-dihydropyridine, the compound prepared according to the invention is described by the following formula I*:

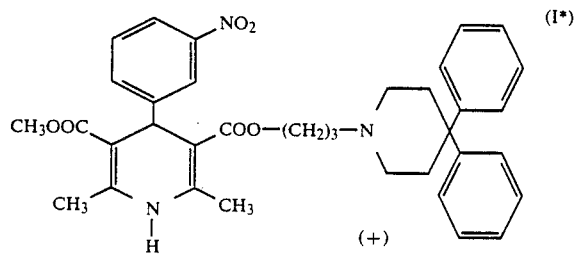

In this case, the process is characterised in that an N-protected dihydropyridinecarboxylic acid of the formula II*

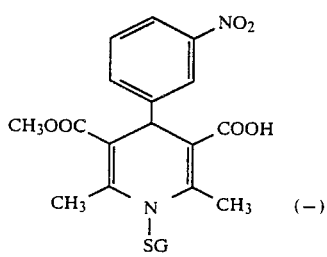

is reacted with 1,3-dibromopropane and, after elimination of the protective group SG, the resulting bromopropyl ester III*

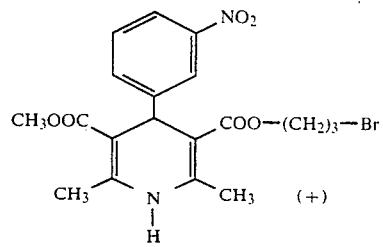

is reacted with diphenylpiperidine or a salt thereof to give the end product I*, and if desired, a resulting salt of compound I* is converted into the free base or the compound I* is converted into a salt.

The process according to the invention can likewise be used for the preparation of 3-methyl 5-[3-(4,4-diphenylpiperid-1-yl)-propyl] (−)-1,4-dihydro-2,6-dimethyl-4-(3-nitrophenyl)-pyridine-3,5-dicarboxylate and its salts, by starting from the optical antipode of compound II*.

Some of the pure enantiomeric compounds of the formula II or II* are known [Chem. Pharm. Bull. 28(9) 2809–2812 (1980)] and some are novel. They can be prepared in a known manner [Chem. Pharm. Bull. 28(9) 2809–2812 (1980)] or by a novel process.

The novel process is characterised in that the protective group SG is introduced into haloethyl esters of the formula V (Hal=chlorine, in particular bromine)

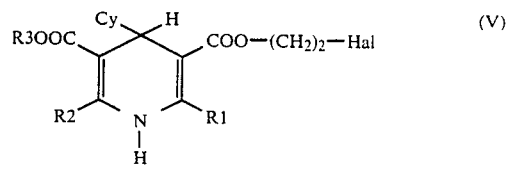

Hal is exchanged for a nucleophile acting as an acceptor (=Akz) in the resulting N-protected haloethyl ester of the formula VI

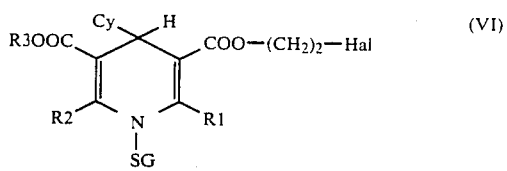

the acceptor ethyl radical is eliminated from the resulting acceptor ethyl ester of the formula VII

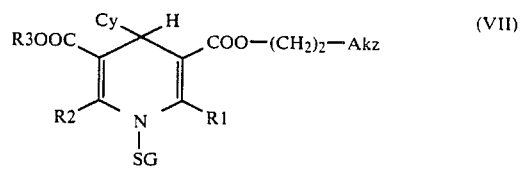

under basic conditions and the resulting racemate of the compound II is resolved into the enantiomers.

To introduce the protective group SG, it is advantageous to adopt a procedure in which the haloethyl ester V is deprotonated in the 1-position and then reacted with a compound SG-X, where X represents a suitable leaving group.

Particularly suitable deprotonating agents are agents for which the acidity of the proton on the nitrogen is sufficiently high to achieve anion formation. In addition to organometallic compounds, such as, for example, butyllithium, metal hydrides, in particular sodium hydride, may be preferably mentioned. The leaving group X of the compound SG-X is a group which is readily eliminated in the reaction of SG-X with the deprotonated V. If the protective group SG is an alkoxymethyl group, X is preferably a halogen atom, in particular a chlorine atom.

The deprotonation and subsequent introduction of the protective group is carried out in inert anhydrous solvents, as are suitable for use with strong deprotonating agents. Open-chain or cyclic ethers, such as diethyl ether, dioxane or tetrahydrofuran may be mentioned as examples. The reaction is preferably carried out under mild reaction conditions at temperatures of about or below 0° C.

Particularly suitable acceptor radicals in the further reaction are radicals which can have a mesomeric electron-attracting effect. The nitro group or the azido group, preferably the nitrile group or a substituted sulphonyl group, may be mentioned as examples.

Halogen exchange in the N-protected haloethyl ester of the formula VI is preferably carried out by reaction with salts whose anions are capable of acting as covalently bonded acceptor substitutes. A preferred reaction is the reaction with inorganic cyanides, in particular with potassium cyanide or sodium cyanide, or the reaction with alkali metal sulphinates, in particular with sodium 4-toluenesulphinate, if desired with the addition of catalytic amounts of a quaternary ammonium salt, such as, for example, tetrabutylammonium cyanide or benzyltriethylammonium chloride, in inert, preferably aprotic, polar solvents, such as, for example, acetone, dimethyl sulphoxide or dimethylformamide, at temperatures which are preferably between 0° C. and 50° C.

The elimination of the acceptor ethyl radical under basic conditions, which follows the halogen exchange is a reaction which is familiar to the skilled worker and is described in, for example. German Offenlegungsschrift 2,847,237. The compound II, which is initially obtained as a racemate, can be resolved into the enantiomers (+)-II and (−)-II with the aid of pure enantiomeric, optically active bases in a conventional manner via the diastereomeric salts [see, for example, Chem. Pharm. Bull. 23 2809 (1980)][1].

Cinchonidine and cinchonine may be mentioned in particular as pure enantiomeric, optically active bases.

The haloethyl esters V used as starting compounds are disclosed, for example, in German Offenlegungsschrift 2,847,237.

The preparation examples which follow are intended to illustrate the invention in detail without restricting it. Mp. denotes melting point, h represents hours, b.p. represents boiling point and decomp. denotes decomposition. Ether is understood as being diethyl ether.

EXAMPLES End Products 1. 3-Methyl 5-{3-[4-(2-methoxyphenyl)-1-piperazinyl]-propyl}(+)-1,4-dihydro-2,6-dimethyl-4-(3-nitrophenyl)-pyridine-3,5-dicarboxylate 3.7 g of 3-methyl 5-(3-bromopropyl) (+)-1,4-dihydro-2,6-dimethyl-4-(3-nitrophenyl)-pyridine-3,5-dicarboxylate, 1.8g of 1-(2-methoxyphenyl)-piperazine semicarbonate and 3.4 g of potassium carbonate in a mixture of 35 ml of toluene and 10 ml of water are refluxed for 9 hours under a nitrogen atmosphere with vigorous stirring. After cooling, the phases are separated, and the organic phase is washed neutral with water, dried over sodium sulphate and evaporated in vacuo. The residue is crystallised from ethyl acetate/diisopropyl ether. After filtration under suction, washing with diisopropyl ether and drying in vacuo, 3.4 g of the title compound of m.p. 139°–140° C. and $[\alpha]^{22}_D = +16.9°$ (c=1, methanol) are obtained.

2. 3-Ethyl 5-[3-(4,4-diphenyl-1-piperidinyl)-propyl] (+)-1,4-dihydro-2,6-dimethyl-4-(3-nitrophenyl)-pyridine-3,5-dicarboxylate hydrochloride 2 g of (+)-5-ethoxycarbonyl-1-ethoxymethyl-1,4-dihydro-2,6-dimethyl-4-(3-nitrophenyl)-pyridine-3-carboxylic acid are dissolved in 25 ml of acetone, and 1.5 g of finely powdered potassium carbonate, 7.5 ml of 1,3-dibromopropane and a spatula tip of [18]crown-6 are added. The mixture is stirred vigorously for 20 h at room temperature, after which the solution is filtered off from the solid, the filtrate is evaporated in vacuo and the excess 1,3-dibromopropane is distilled off under high vacuum. 15 ml of concentrated formic acid are added to the residue while cooling with ice; stirring is then carried out at room temperature until a clear solution has formed (about 15–20 minutes). The formic acid is distilled off in vacuo, the residue is dissolved in 30 ml of dichloromethane and the solution is washed with sodium bicarbonate solution and water, dried over sodium sulphate and evaporated again. The crystalline residue is triturated with diisopropyl ether, filtered off under suction, washed with diisopropyl ether and dried. 2.2 g are obtained and are heated at the boil, without further purification, with 1.32 g of 4,4-diphenylpiperidine hydrochloride and 2 g of potassium carbonate in a mixture of 20 ml of toluene and 4 ml of water for 30 h. After cooling, the phases are separated. The organic phase is washed twice with water and evaporated. The residue is chromatographed over a silica gel column using 95:5 chloroform/ethanol as the mobile phase. The chromatographically pure fractions are collected and evaporated. The residue is dissolved in dichloromethane, 2 ml of a saturated solution of hydrogen chloride in ether are added and the mixture is immediately evaporated in vacuo. Two portions of 20 ml of dichloromethane are distilled off, after which the residue is triturated with ether, filtered off under suction and dried. 2.65 g of the title compound which decomposes from 142° C. and has $[\alpha]^{22}_D = +18.9°$ (c=1, methanol) are obtained.

3. 3-Methyl 5-3-(4,4-diphenylpiperid-1-yl)-propyl] (−)-4-(2,3-dichlorophenyl)-1,4-dihydro-2,6-dimethylpyridine-3,5-dicarboxylate hydrochloride 1.3 8 of (+)-4-(2,3-dichlorophenyl)-1-ethoxymethyl-1,4-dihydro-2,6-dimethyl-5-methoxycarbonylpyridine-3-carboxylic acid are dissolved in 15 ml of acetone, 1 g of finely powdered potassium carbonate, 5 ml of 1,3-dibromopropane and a spatula tip of [18]crown-6 are added and vigorous stirring is carried out for 20 h. The solution is filtered off under suction from the solid, the filtrate is evaporated in vacuo and the excess 1,3-dibromopropane is distilled off under high vacuum. 10 ml of concentrated formic acid are added to the residue while cooling with ice; stirring is then carried out at room temperature until a clear solution has formed (about 15–20 minutes). The formic acid is distilled off in vacuo, the residue is dissolved in 20 ml of dichloromethane and the solution is washed with sodium bicarbonate solution and water, dried over sodium sulphate and evaporated down. The residue is dried under high vacuum. The solid foam (1.2 g) is heated at the boil, without further purification, with 0.68 g of 4,4-diphenylpiperidine hydrochloride and 1 g of potassium carbonate in a mixture of 15 ml of toluene and 5 ml of water for 21 h. After cooling, the phases are separated. The organic phase is washed twice with water and evaporated. The residue is chromatographed over a silica gel column using 95:5 chloroform/ethanol as the mobile phase. The chromatographically pure fractions are collected and evaporated. The remaining oil is dissolved in 20 ml of dichloromethane, 2 ml of a saturated solution of hydrogen chloride in ether are added to the solution and the mixture is immediately evaporated in vacuo. Two 20 ml portions of dichloromethane are distilled off, after which the residue is triturated with ether, filtered off under suction, washed with ether and dried. 1.3 g of the title compound which decomposes from 160° C. and has $[\alpha]^{22}_D = -41.4°$ (c=1, methanol) are obtained.

4. 3-Methyl 5-[3-(4,4-diphenylpiperid-1-yl)-propyl] (+)-1,4-dihydro-2,6-dimethyl-4-(3-nitrophenyl)-pyridine-3,5-dicarboxylate hydrochloride A mixture of 13 g of 3-methyl 5-(3-bromopropyl) (+)-1,4-dihydro-2,6-dimethyl-4-(3-nitrophenyl)-pyridine-3,5-dicarboxylate, 7.85 g of 4,4-diphenylpiperidine hydrochloride and 12 g of potassium carbonate in 120 ml of toluene and 25 ml of water is refluxed for 14 h under a nitrogen atmosphere and with vigorous stirring. After cooling, the phases are separated; the organic phase is washed twice with water, dried over sodium sulphate and evaporated in vacuo. The oily residue is dissolved in 140 ml of dioxane, after which 2.3 ml of concentrated hydrochloric acid solution (12.5 M, d=1.19) are added and 20-25 ml of the solvent mixture are then distilled off in vacuo. On standing at room temperature, the product crystallises spontaneously or after trituration and is filtered off under suction after 16 h, washed with dioxane and diisopropyl ether and dried in vacuo at 80° C. 16 g of the title compound of m.p. 158°-160° C. and $[\alpha]^{22}_D = +14.4°$ (c=1, methanol) are obtained.

5. 3-Methyl 5-[3-(4,4-diphenyl-1-piperidinyl)-propyl] (−)-1,4-dihydro-2,6-dimethyl-4-(3-nitrophenyl)-pyridine-3,5-dicarboxylate hydrochloride 86.6 g of 3-methyl 5-(3-bromopropyl) (−)-1,4-dihydro-2,6-dimethyl-4-(3-nitrophenyl)-pyridine-3,5-dicarboxylate, 50 g of 4,4-diphenylpiperidine hydrochloride and 69 g of finely milled potassium carbonate are heated together in 300 ml of dimethylformamide for 5 h at 100° C. with vigorous stirring and under a nitrogen atmosphere. After cooling, 500 ml of ethyl acetate and 1 l of water are added in succession and the mixture is stirred thoroughly. After phase separation, the organic phase is washed 4 times with water, dried over sodium sulphate and evaporated in vacuo. The residue is dissolved in 1 l of dioxane and 15.2 ml of concentrated hydrochloric acid solution (12.5 M, d=1.19) are added to the cooled solution; about 200 ml of the solvent mixture are then distilled off in vacuo. On standing at room temperature, the product crystallises spontaneously or after seeding or trituration; it is filtered off under suction after 16 h, washed with dioxane and diisopropyl ether and dried in vacuo at 80°-100° C. For purification, the product is dissolved in dichloromethane. After the addition of 800 ml of dioxane, the dichloromethane is distilled off again. The product which has crystallised out after seeding and standing at room temperature for 16 hours is filtered off under suction, washed with dioxane and diisopropyl ether and dried at 100° C. 97 g of the title compound of m.p. 158°-160° C. and $[\alpha]^{22}_{436} = -39°$ (c=1, methanol) or $[\alpha]^{22}_D = -14.4°$ (c=1, methanol) are obtained.

6. 3-Methyl 5-[2-(4,4-diphenyl-1-piperidinyl)-ethyl] (+)-1,4-dihydro-2,6-dimethyl-4-(3-nitrophenyl)-pyridine-3,5-dicarboxylate hydrochloride 2.35 g of 3-methyl 5-(2-bromoethyl) (+)-1,4-dihydro-2,6-dimethyl-4-(3-nitrophenyl)-pyridine-3,5-dicarboxylate, 1.46 g of 4,4-diphenylpiperidine hydrochloride and 1.55 g of finely powdered potassium carbonate in 15 ml of anhydrous dimethylformamide are stirred for 6 h at 80° C. After the mixture has cooled, 100 ml of water are added and the mixture is then extracted with ether. The ether phase is washed twice with water, dried over sodium sulphate and then evaporated in vacuo. The residue is chromatographed over a silica gel column using a 95:5 chloroform/ethanol as the mobile phase. The chromatographically pure fractions are collected and evaporated. The residue is dissolved in ether and 2 ml of a saturated solution of hydrogen chloride in ether are added to the solution, crystallisation occurring. The product is filtered off under suction, washed with ether and dried. 1.4 g of the title compound of m.p. 155°-158° C. (decomp.) and $[\alpha]^{22}_D = +68.4°$ (c=1, methanol) are obtained.

7. 3-Methyl 5-[2-(4-phenyl-1-piperidinyl)-ethyl] (+)-1,4-dihydro-2,6-dimethyl-4-(3-nitrophenyl)-pyridine-3,5-dicarboxylate Analogously to Example 6, 2.9 g of the title compound of m.p. 129°-131° C. (decomp.) and $[\alpha]^{21}_D = +40.8°$ (c=1, methanol) are obtained from 5 g of 3-methyl-5-(2-bromoethyl)+)-1,4-dihydro-2,6-dimethyl-4-(3-nitrophenyl)-pyridine-3,5-dicarboxylate, 1.9 g of 4-phenylpiperidine and 4.4 g of diisopropylethylamine after chromatography and crystallisation from 2-propanol.

8. 3-Methyl 5-[3-(4-phenyl-1-piperidinyl)-propyl] (+)-1,4-dihydro-2,6-dimethyl-4-(3-nitrophenyl)-pyridine-3,5-dicarboxylate hydrochloride Analogously to Example 6. 3.4 g of the title compound which decomposes from 100° C. and has $[\alpha]^{21}_D = +41.7°$ (c=1, methanol) are obtained from 5 g of 3-methyl-5-(3-bromopropyl) (+) 1,4-dihydro-2,6-dimethyl-4-(3-nitrophenyl)-pyridine-3,5-dicarboxylate, 1.9 g of 4-phenylpiperidine and 4.4 g of diisopropylethylamine.

9. 3-Methyl 5-{3-[4-(2-ethoxy-4-fluorophenyl)-1-piperazinyl]-propyl}(+)-1,4-dihydro-2,6-dimethyl-4-(3-nitrophenyl)-pyridine-3,5-dicarboxylate Analogously to Example 6, 2.1 g of the title compound of m.p. 150°-152° C. and $[\alpha]^{22}_D = +14.4°$ (c=1, methanol) are obtained from 3 g of 3-methyl-5-bromopropyl (+)-1,4-dihydro-2,6-dimethyl-4-(3-nitrophenyl)-pyridine-3,5-dicarboxylate, 2 g of 1-(2-ethoxy-4-fluorophenyl)-piperazine dihydrochloride and 3.7 g of finely powdered potassium carbonate in 20 ml of absolute dimethylformamide after chromatography and crystallisation from 2-propanol.

10. 3-Methyl 5-[2-(4-benzhydryl-1-piperazinyl)-ethyl] (+)-1,4-dihydro-2,6-dimethyl-4-(3-nitrophenyl)-pyridine-3,5-dicarboxylate dihydrochloride Analogously to Example 6. 3.2 g of the title compound which decomposes from 210° C. and has $[\alpha]^{21}_D = +52.1°$ (c=1, methanol) are obtained from 4 g of 3-methyl-5-(2-bromoethyl) (+)-1,4-dihydro-2,6-dimethyl-4-(3-nitrophenyl)-pyridine-3,5-dicarboxylate and 6.5 g of 1-benzhydrylpiperazine after chromatography and conversion into the dihydrochloride.

11. 3-Methyl 5-[3-(4-benzhydryl-1-piperazinyl)-propyl] (+)-1,4-dihydro-2,6-dimethyl-4-(3-nitrophenyl)-pyridine-3,5-dicarboxylate dihdydrochloride Analogously to Example 6. 4 g of the title compound which decomposes from 170° C. and has $[\alpha]^{22}_D = +35.2°$ (c=1, methanol) are obtained from 4.5 g of 3-methyl-5-(3-bromopropyl) (+)-1,4-dihydro-2,6-dimethyl-4-(3-nitrophenyl)-pyridine-3,5-dicarboxylate, 2,6 g of 1-benzhydrylpiperazine and 2.8 g of finely powdered potassium carbonate after chromatography and conversion into the dihydrochloride.

STARTING COMPOUNDS A. 3-Methyl 5-(3-bromopropyl]{+)-1,4-dihydro-2,6-dimethyl-4-(3-nitrophenyl)-pyridine-3,5-dicarboxylate 36 g of (−)-1-ethoxymethyl-1,4-dihydro-5-methoxycarbonyl-2,6-dimethyl-4-(3-nitrophenyl)-pyridine-3-carboxylic acid cinchonidine salt are dissolved in 250 ml of chloroform, 260 ml of 0.2 N hydrochloric acid solution are added and the mixture is stirred vigorously. By adding 2 N hydrochloric acid solution, the pH is adjusted to 2, after which the phases are separated. The organic phase is washed a total of 4 times with hydrochloric acid solution at pH 2 and then with water, dried over sodium sulphate and evaporated. The oily residue is dissolved in 200 ml of acetone. Thereafter, 16 g of finely powdered potassium carbonate, 80 ml of 1,3-dibromopropane and 0.5 g of [18]crown-6 are added. The mixture is stirred vigorously for 16 h at room temperature and then filtered under suction, and the filter cake is washed with acetone. The acetone is stripped off in a rotary evaporator under a slight vacuum and the excess 1,3-dibromopropane is distilled off at 0.02 mbar. 160 ml of concentrated formic acid is poured over the oily residue while cooling with ice; stirring is then carried out at room temperature until a clear solution is formed (about 15 minutes). The formic acid is distilled off in vacuo. After two 50 ml portions of toluene have been added and distilled off, the residue is dissolved in dichloromethane. The solution is stirred thoroughly with sodium bicarbonate solution (pH 8.5). The organic phase is dried over sodium sulphate and evaporated. The oily residue is then crystallised from methanol at room temperature. 18.9 g of the title compound of m.p. 112°–114° C. and $[\alpha]^{22}_D = +13.8°$ (c=1, methanol) are obtained.

8. (−)-1-Ethoxymethyl-1,4-dihydro-5-methoxycarbonyl-2,6-dimethyl-4-(3-nitrophenyl)-pyridine-3-carboxylic acid cinchonidine salt 229.7 g of (±)-1-ethoxymethyl-1,4-dihydro-5-methoxycarbonyl-2,6-dimethyl-4-(3-nitrophenyl)-pyridine-3-carboxylic acid and 173.2 g of cinchonidine are dissolved in 2.4 l of ethanol at elevated temperatures. On slow cooling, the title compound crystallises out and, after standing at room temperature for 2 days, is filtered off under suction and washed with ethanol. Recrystallisation twice from ethanol gives 148 g of the title compound of m.p. 185°–185.5° C. and $[\alpha]^{22}_D = -63.4°$ (c=1, chloroform). By working up the mother liquor from the first crystallisation, the corresponding (+)-enantiomer can be obtained:

The mother liquor is evaporated to dryness in vacuo, the residue is dissolved in 2 l of chloroform, 1 l of water is added while stirring vigorously and a stable of 2 to 3 is then obtained by the dropwise addition of 2 N hydrochloric acid. The phases are separated and the organic phase is extracted by shaking with 0.01 N hydrochloric acid until cinchonidine is no longer detectable (thin-layer chromatography) and is washed with water and dried. After the solvent has been distilled off in vacuo the residue is dried under high vacuum and 85.6 g thereof are dissolved together with 54.5 g of cinchonine in about 2.4 l of boiling ethanol. The product which has crystallised out after standing for 3 days at room temperature is filtered off under suction, washed with ethanol and once again recrystallised from ethanol. 88.5 g of (+)-1-ethoxymethyl-1,4-dihydro-5-methoxycarbonyl-2 6-dimethyl-4-(3-nitrophenyl)-pyridine-3-carboxylic acid cinchonine salt of m.p. 197°–198° C. and $[\alpha]^{22}_D = +101.5°$ (c=1, methanol) are obtained.

C. (±)-1-Ethoxymethyl-1,4-dihydro-5-methoxycarbonyl-2,6-dimethyl-4-(3-nitrophenyl)-pyridine-3-carboxylic acid (a) 195.5 g of 3-methyl 5-(2-bromoethyl) (±)-1-ethoxymethyl-1,4-dihydro-2,6-dimethyl-4-(3-nitrophenyl)-pyridine-3,5-dicarboxylate are dissolved in 900 ml of dimethylformamide, and 40.6 g of powdered sodium cyanide and 0.5 g of tetrabutylammonium cyanide are added. The mixture is stirred for 26 h at room temperature, a thick precipitate separating out after about 4 h, after which 200 ml of 2 N sodium hydroxide solution are added dropwise and stirring is continued for 5 h at room temperature. The mixture is stirred into 4.5 l of water and 2 N hydrochloric acid solution are added dropwise, while cooling and stirring vigorously, until the pH reaches 2.5. The product precipitated during this procedure is filtered off under suction rapidly, washed neutral with water, dried in the air overnight and then heated in 400 ml of ethanol on a steam bath (no solution). It is left to stand for 12 h at room temperature, then cooled, filtered off under suction and dried. 142 g of the title compound of m.p. 176°–176.5° C. (decomposition) are obtained.

(b) 5 g of 3-methyl 5-(2-bromoethyl) (±)-1-ethoxymethyl-1,4-dihydro-2,6-dimethyl-4-(3-nitrophenyl)-pyridine-3,5-dicarboxylate are dissolved in 35 ml of dimethylformamide, 3.55 g (20 mmol) of sodium 4-toluenesulphinate and 0.1 g of benzyltriethylammonium chloride are added and the mixture is stirred for 20 h at 20° C. 11 ml of 2 N sodium hydroxide solution are added, the mixture is stirred for 5 h at 20° C. and for a further 3 h at 80° C. and is cooled and then poured onto 120 ml of ice water. After the addition of acetic acid until a pH of 3.8 is obtained, stirring is carried out for 3 h in an ice bath, the solution is filtered off from the precipitated solid and the solid is washed neutral with water and dried. The crude product is boiled in 10 ml of ethanol, cooled, filtered and dried. 3.3l g of the title compound of m.p. 176°–176.5° C. (decomp.) are obtained.

D. 3-Methyl 5-(2-bromoethyl) (±)-1-ethoxymethyl-1,4-dihydro-2,6-dimethyl-4-(3-nitrophenyl)-pyridine-3,5-dicarboxylate 10.65 g of a 80% suspension of sodium hydride in liquid paraffin are suspended in 300 ml of anhydrous tetrahydrofuran. A solution of 120 g of 3-methyl 5-(2-bromoethyl) (±)-1,4-dihydro-2,6-dimethyl-4-(3-nitrophenyl)-pyridine-3,5-dicarboxylate and 28.4 g of chloromethyl ethyl ether in 300 ml of anhydrous tetrahydrofuran is slowly added dropwise in the course of 4 h at −5° to −7° C., while stirring. After the mixture has been stirred for a further hour at 0° C., 600 ml of toluene and 210 ml of water are added in succession. The phases are separated, and the organic phase is washed with water, dried overnight and evaporated in vacuo. The residue is dissolved in 390 ml of warm ethanol and the stirred solution is then cooled. The product crystallises out during this procedure. It is cooled to 0° C., filtered off under suction, washed with ice-cold ethanol and dried. 98.5 g of the title compound of m.p. 72.5°–74° C. are obtained.

E. 3-Methyl 5-(2-bromoethyl) (±(-1,4-dihydro-2,6-dimethyl-4-(3-nitrophenyl)-pyridine-3,5-dicarboxylate 494 g of 2-bromoethyl 2-(3-nitrobenzylidene)-acetoacetate and 173.5 g of methyl 3-aminocrotonate are dissolved in 1750 ml of isopropanol at 75–80° C. while stirring and under a nitrogen atmosphere. The mixture is then cooled very slowly in a heating bath. The mixture is seeded with the title compound, after which it is stirred for 16 h at room temperature and then cooled, and the product is filtered off under suction, washed with ice-cold ether and dried. 481 g of the title compound of m.p. 139°–141° C. are obtained.

F. 2-Bromoethyl 2-(3-nitrobenzylidene)-acetoacetate 405 g of 2-bromoethyl acetoacetate are dissolved in 1500 ml of isopropanol. 293 g of 3-nitrobenzaldehyde, 4.6 g of acetic acid and 6.8 g of piperidine are added while stirring. The mixture is stirred at 40° C. until a clear solution has formed. The solution is allowed to cool slowly, seeded with a few crystals of the title compound and stirred at room temperature for 48 h and then cooled, and the product is filtered off under suction, washed with cold isopropanol and dried in vacuo at 50° C. 495 g of the title compound of m.p. 94.5°–95.5° C. are obtained.

G. 2-Bromoethyl acetoacetate 250 g of 2-bromoethanol are dissolved in 1.3 l of dichloromethane, and 1.2 g of 4-dimethylaminopyridine are added. 400 ml of a 50% strength diketene solution in acetone are added dropwise with vigorous stirring, so that the solvent boils moderately. After the dropwise addition, stirring is continued for a further 1 h at the boiling point and the mixture is then left to stand overnight. After the solvent has been evaporated off in a rotary evaportor in vacuo, the residue is distilled. 402 g of the title compound of b.p. 80°–83° C./0.04 mbar are obtained.

H. (+)-4-(2,3-dichlorophenyl)-1-ethoxymethyl-1,4-dihydro-2,6-dimethyl-5-methoxycarbonylpyridine-3-carboxylic acid 9.5 g of (±)-4-(2,3-dichlorophenyl)-1-ethoxymethyl-1,4-dihydro-2,6-dimethyl-5-methoxycarbonylpyridine-3-carboxylic acid and 6.75 g of cinchonidine are dissolved in 50 ml of methanol at the boil; the hot solution is filtered and then cooled. After seeding, the mixture is allowed to stand for several days at 0°–4° C., after which the product is filtered off under suction, washed with cold methanol and again recrystallised from methanol. 4.85 g of the cinchonidine salt of the title compound of m.p. 176°–178° C. are obtained. The salt is dissolved in 60 ml of chloroform. After the addition of 30 ml of water, the aqueous phase is adjusted to a pH of 2 by the addition of 2 N hydrochloric acid solution with vigorous stirring. After phase separation, the organic phase is washed 4 times with 0.01 N hydrochloric acid and once with water, dried over sodium sulphate and then evaporated in vacuo. The remaining crystalline residue is dried under high vacuum. 3.1 g of the title compound of m.p. 129°–131° C. and $[\alpha]^{22}_D = +63.2°$ (c=1, chloroform) are obtained.

I. (±)-4-(2,3-Dichlorophenyl)-1-ethoxymethyl-1,4-dihydro-2,6-dimethyl-5-methoxycarbonylpyridine-3-carboxylic acid Analogously to Example C, 9.5 g of the title compound of m.p. 156°–157° C. (from ethanol) are obtained from 14.25 g of 3-(2-bromoethyl) 5-methyl (±)-4-(2,3-dichlorophenyl)-1-ethoxymethyl-1,4-dihydro-2,6-dimethylpyridine-3,5dicarboxylate, 2.8 g of powdered sodium cyanide and a spatula tip of tetrabutylammonium cyanide in 60 ml of dimethylformamide after the addition of ml of 2 N sodium hydroxide solution and identical working up.

J. 3-(2-bromoethyl) 5-methyl (±)-4-(2,3-dichlorophenyl)-1-ethoxymethyl-1,4-dihydro-2,6-dimethylpyridine-3,5-dicarboxylate Analogously to Example D, 14.3 g of the title compound of m.p. 104°–106° C. (from methanol) are obtained from 19.1 g of 3-(2-bromoethyl) 5-methyl (±)-4-(2,3-dichlorophenyl)-1,4-dihydro-2,6-dimethylpyridine-3,5-dicarboxylate, 1.64 g of sodium hydride (80% in liquid paraffin), 4.75 g of chloromethyl ethyl ether and twice 50 ml of anhydrous tetrahydrofuran.

K. 3-(2-Bromoethyl) 5-methyl (±)-4-(2,3-dichlorophenyl)-1,4-dihydro-2,6-dimethyl-pyridine-3,5-dicarboxylate 50 g of 2,3-dichlorobenzaldehyde and 60 g of 2-bromoethyl acetoacetate are dissolved in 400 ml of dichloromethane. 0.83 ml of glacial acetic acid, 1,4 ml of piperidine and 30 g of anhydrous sodium sulphate are added to the solution. The mixture is stirred for 4 days at room temperature, a further 20 g of anhydrous sodium sulphate being added after 2 days. After filtration under suction, the solution is washed with water. 0.1 N hydrochloric acid, dilute sodium bicarbonate solution and again with water and dried over sodium sulphate. After the solvent has been distilled off in vacuo, the oil residue is dissolved in 600 ml of tetrahydrofuran, and 33 g of methyl 3-aminocrotonate are added to the solution. The mixture is heated at the boil for 24 hours with nitrogen and cooled, after which the solvent is distilled off in vacuo, the residue is dissolved in dichloromethane and the solution is washed with 0.01 N hydrochloric acid and water. After drying over sodium sulphate, it is evaporated again. 150 ml of 2-propanol are added to the partially crystalline residue, the mixture is cooled and the product is filtered off under suction. Recrystallisation from 2-propanol gives 79 g of the title compound of m.p. 180°–182° C.

L.
(+)-5-Ethoxycarbonyl-1-ethoxymethyl-1,4-dihydro-2,6-dimethyl-4-(3-nitrophenyl)-pyridine-3-carboxylic acid 37.5 g of (±)-5-ethoxycarbonyl-1-ethoxymethyl-1,4-dihydro-2,6-dimethyl-4-(3-nitrophenyl)-pyridine-3-carboxylic acid and 27.3 g of cinchonidine are dissolved in 450 ml of ethanol at the boil and then cooled slowly while stirring. After the mixture has been stirred for five days, it is filtered under suction and the residue is washed with ethanol and recrystallised 4 times from ethanol. The salt thus obtained (18.3 g) is dried and then dissolved in 300 ml of chloroform. After the addition of 150 ml of water, the pH is adjusted to 2 with 2 N hydrochloric acid solution while stirring vigorously. After phase separation, the organic phase is extracted by shaking 4 times with 0.01 N hydrochloric acid solution until cinchonidine can no longer be detected by thin-layer chromatography. It is washed neutral, dried over sodium sulphate and then evaporated, and the crystalline residue is dried under high vacuum. 10.6 g of the title compound of m.p. 133° C. (decomp.) and $[\alpha]^{22}_D = +82.5°$ (c=1, chloroform) are obtained.

M.
(±)-5-Ethoxycarbonyl-1-ethoxymethyl-1,4-dihydro-2,6-dimethyl-4-(3-nitrophenyl)-pyridine-3-carboxylic acid 53.9 g of 3-ethyl 5-(2-bromoethyl) (±)-1-ethoxymethyl-1,4-dihydro-2,6-dimethyl-4-(3-nitrophenyl)-pyridine-3,5-dicarboxylate are dissolved in 190 ml of dimethylformamide, and 10.85 g of powdered sodium cyanide and a spatula tip of tetrabutylammonium cyanide are added. After the mixture has been stirred for 60 h at room temperature. 110 ml of 2 N sodium hydroxide solution are added dropwise. After it has been stirred for a further 3 h, the mixture is stirred into 2 l of water. The pH is adjusted to 3 by the dropwise addition of 2 N hydrochloric acid solution while cooling with ice. The precipitate which separates out during this procedure is filtered off under suction, washed neutral with water and dried. For purification, it is boiled with 90 ml of ethanol, cooled, filtered off under suction and washed with cold ethanol. Following drying, 37.5 g of the title compound of m.p. 181°–182° C. (decomp.) are obtained.

N. 3-Ethyl 5-(2-bromoethyl) (±)-1-ethoxymethyl-1,4-dihydro-2,6-dimethyl-4-(3-nitrophenyl)-pyridine-3,5-dicarboxylate Analogously to starting compound D, 53.9 g of the title compound of m.p. 102°–104° C. (ethanol) are obtained from 64.9 g of 3-ethyl 5-(2-bromoethyl) (±)-1,4-dihydro-2,6-dimethyl-4-(3-nitrophenyl)-pyridine-3,5-dicarboxylate, 5.2 g of sodium hydride (80% in liquid paraffin), 14.9 g of chloromethyl ethyl ether and twice 130 ml of tetrahydrofuran.

O. 3-Ethyl 5-(2-bromoethyl) (±)-1,4-dihydro-2,6-dimethyl-4-(3-nitrophenyl)-pyridine-3,5-dicarboxylate 58.8 g of 2-bromoethyl 2-(3-nitrobenzylidene)-acetoacetate and 22.5 g of ethyl 3-aminocrotonate in 250 ml of tetrahydrofuran are heated at the boil for 3 h. The mixture is stirred for 8 h at room temperature, after which the solvent is distilled off in vacuo and the solid residue is dissolved in hot 2-propanol. The title compound crystallises out on cooling. It is filtered off under suction, washed with cold 2-propanol and dried. 65 g of product of m.p. 158°–159° C. are obtained.

P. 3-Methyl 5-(3-bromopropyl) (−)-1,4-dihydro-2,6-dimethyl-4-(3-nitrophenyl)-pyridine-3,5-dicarboxylate 168.5 g of (+)-1-ethoxymethyl-1,4-dihydro-5-methoxycarbonyl-2,6-dimethyl-4-(3-nitrophenyl)-pyridine-3-carboxylic acid cinchonine salt $\{[\alpha]^{22}_D = +101.5°$ (c=1, chloroform)$\}$ (prepared from (±)-1-ethoxymethyl-1,4-dihydro-5-methoxycarbonyl-2,6-dimethyl-4-(3-nitrophenyl)-pyridine-3-carboxylic acid and cinchonine analogously to Example B) are dissolved in 1.5 l of dichloromethane, after which 1.2 l of 0.2 N hydrochloric acid solution are added while cooling and stirring vigorously. By adding 2 N hydrochloric acid solution, a stable pH of 2 is obtained in the aqueous phase. After phase separation, the organic phase is washed four times with hydrochloric acid solution of pH 2 and then with water, dried over sodium sulphate and then evaporated. The oily residue is dissolved in 1.1 l of acetone, and 375 g of finely milled potassium carbonate, 375 ml of 1,3-dibromopropane and 1.2 g of [18]crown-6 are added. The mixture is stirred vigorously for 24 h at room temperature, then filtered under suction and the filter cake is washed with acetone. The filtrate is evaporated in a rotary evaporator under a slight vacuum, after which the excess 1,3-dibromopropane is distilled off at 0.02 mbar (bath temperature up to 45° C.). 690 ml of concentrated formic acid are poured over the oily residue after cooling with ice, after which stirring is carried out at room temperature until a clear solution has formed (about 15 min). The formic acid is distilled off in vacuo. After 200 ml portions of toluene have been added twice and distilled off twice, the residue is dissolved in 900 ml of dichloromethane. The solution is stirred thoroughly with sodium bicarbonate solution, washed with water, dried over sodium sulphate and evaporated in vacuo. The product which spontaneously crystallises after the addition of diisopropyl ether is filtered off under suction, washed with diisopropyl ether and dried in vacuo. 102 g of the title compound of m.p. 112°–114° C. and $[\alpha]^{22}_D = -13.8°$ (c=1, methanol) are obtained.

Q. 3-Methyl 5-(2-bromoethyl) (+)-1,4-dihydro-2,6-dimethyl-4-(3-nitrophenyl)-pyridine-3,5-dicarboxylate Analogously to starting compound A. 8.8 g of (−)-1-ethoxymethyl-1,4-dihydro-5-methoxycarbonyl-2,6-dimethyl-4-(3-nitrophenyl)-pyridine-3-carboxylic acid cinchonidine salt are liberated and then reacted in 60 ml of acetone with 36 g of 1,2-dibromoethane, 3.9 g of finely powdered potassium carbonate and 0.1 g of [18]crown-6. After elimination of the protective group in 50 ml of concentrated formic acid and crystallisation from diisopropyl ether, 4.75 g of the title compound of m.p. 142°–144° C. (decomp.) and $[\alpha]^{22}_D = +31.5°$ (c=1, chloroform) are obtained.

INDUSTRIAL APPLICATION

The pure enantiomeric compounds of the formula I prepared by the process according to the invention, and their salts, have valuable properties which make them industrially useful. They are, for example, effective vasodilators having therapeutic properties against coronary diseases. The pharmacological activity of the compounds according to the invention, which is coupled with low toxicity, is evident, for example, in a slow, pronounced and long-lasting lowering of blood pressure. Moreover, the compounds according to the invention have an inhibitory effect on calcium influx and promote the flow of potassium out of cells, relax smooth muscle, dilate peripheral, coronary, cerebral and renal vessels and have salidiuretic, antithrombotic, antiarteriosclerotic and advantageous haemorheological properties.

In their excellent efficacy, which is coupled with low toxicity and the lack of significant side effects, the enantiomers according to the invention differ in a surprising and advantageous manner from their racemates. Particularly surprising is the fact that the enantiomers according to the invention, which, in the 4-position of the dihydropyridine, have the same configuration as (−)-1-ethoxymethyl-1,4-dihydro-5-methoxycarbonyl-2,6-dimethyl-4-(3-nitrophenyl)-pyridine-3-carboxylic acid cinchonidine salt, which can be used as a precursor and rotates linearly polarised light of wavelength 589 nm through $[\alpha]^{22}_D = -63.4°$ (c=1, chloroform), and has substantially more pronounced antihypertensive action than the enantiomers having the mirror-image configuration.

By providing the enantiomers which are particularly efficacious in the main action, on the one hand the stress due to their less efficacious isostereomers, some of which may even have the opposite action or more pronounced side effects, is substantially reduced. On the other hand, the enantiomers which are less efficacious in the abovementioned main (antihypertensive) action can be used for other therapeutic purposes, which were previously not accessible to this class of substances—owing to the main action predominating in the racemates.

The following may be mentioned as examples of advantageous properties of the compound of I: the extent of lowering of blood pressure, the good controllability of the lowering of blood pressure, the surprisingly small, and for repeated administration vanishing, increase in heart rate, the excellent bioavailability, the high therapeutic index, the lack of central side effects, the lack of kinetic interactions with other substances, the absence of development of tolerance, the well balanced physical properties and the high stability.

The excellent efficacy of the compounds according to the invention, of the formula I, and their salts permit their use in human medicine, examples of their indications being primary (essential) and secondary, arterial and pulmonal hypertensions of all severity levels, coronary heart diseases (coronary insufficiency, angina pectoras, myocardial infarction, etc.), peripheral and cerebral circulatory disorders (stroke, temporary cerebral blood-flow disturbances, migraine, giddiness, narrowing of renal arteries, etc.), hypertrophic cardiomyopathy, cardiac insufficiency, disorders due to increased water retention and sodium retention and disorders due to an increased influx of calcium, such as, for example, spasms of organs containing smooth muscle (respiratory tract, gastrointestinal tract, urogenital tract, etc.) and arrhythmia, arteriosclerosis and cell damage of various origins (for example hypoxia).

The invention therefore also relates to a method for the treatment of mammals, in particular humans, suffering from one of the above-mentioned disorders. The method is characterised in that the suffering individual is administered a therapeutically effect and pharmacologically acceptable amount of one or more compounds of the formula I.

The invention furthermore relates to compounds of the formula I for use in the treatment of the stated disorders.

The invention also relates to the use of the compounds of the formula I for the preparation of medicaments which are used for the treatment of the stated disorders.

The invention furthermore relates to medicaments which contain one or more compounds of the general formula I.

The medicaments are prepared by processes known per se and familiar to the skilled worker. The pharmacologically effective compounds (=active ingredients) according to the invention are used either as such or, preferably, in combination with suitable pharmaceutical auxiliaries, in the form of tablets, coated tablets, capsules, suppositories, plasters (for example as TTS), emulsions, suspensions, aerosols, sprays, ointments, creams, gels or solutions, the content of active ingredient advantageously being between 0.1 and 95%.

On the basis of his technical knowledge, the skilled worker knows which auxiliaries are suitable for the desired drug formulations. In addition to solvents, gel formers, suppository bases, tabletting auxiliaries and other excipients, it is possible to use, for example, antioxidants, dispersants, emulsifiers, antifoams, flavourings, preservatives, solubilizers, colorants or, in particular, permeation promoters and complexing agents (for example cyclodextrins).

The active ingredients may be administered orally, rectally, by inhalation or parenterally (in particular perlingually, intravenously or percutaneously).

In general, it has proved advantageous in human medicine to administer the active ingredient or ingredients in a daily dose of about 0.01 to about 10, preferably 0.05 to 5, mg/kg body weight in the case of oral administration, if desired in the form of several, preferably 1 to 4, individual doses, in order to achieve the desired result. In the case of parenteral treatment, similar or (in particular in the case of intravenous administration of the active ingredient) as a rule lower doses may be used. In the case of increasing dosage, a low dose is administered at the beginning of the treatment, after which higher doses are slowly introduced. After the desired therapeutic success has been attained, the dose is returned to a lower level.

The particular required optimal dose and mode of administration of the active ingredients can easily be determined by any skilled worker on the basis of his technical knowledge.

If the compounds according to the invention and/or their salts are used for the treatment of the stated disorders, the pharmaceutical formulations may also contain one or more other pharmacologically active constituents of other groups of medicaments, such as other vasodilators, antihypertensive agents, alpha-1-receptor blockers, alpha-2-receptor stimulators, beta-1-receptor blockers, beta-2-receptor stimulators. ACE inhibitors, nitro compounds, cardio tonic agents, diuretics, saluretics, alkaloids, analgesics, lipid-lowering agents, anticoagulants, anticholinergic agents, methylxanthines, antiarrhythmics, antihistamines, dopamine stimulators, serotonine receptor blockers, etc., such as nifedipine dihydralazine prazosine, clonidine, atenolol, labetalol, fenoterol, captopril, isosorbide dinitrate, digoxin, milrinone, mefruside, clopamide, spironolactone, chlorthalidone, furosemide, polythiazide, hydrochlorothiazide, reserpine, dihydroergocristine, rescinnamine, rauwolfia total alkaloids, acetylsalicylic acid, bezafibrate, warfarin, atropine, theophylline, lidocaine, astemizole, bromocryptine, ketanserine, etc.

PHARMACOLOGY

The antihypertensive activity of the compounds according to the invention can be demonstrated in the model of the spontaneously hypertensive rat.

For determination of the antihypertensive action, the compounds mentioned below are administered in the stated doses, on four successive days, to 6 male rats (strain SHR/N/Ibm/Bm, 250-350 g) with genetic high blood pressure (systolic high blood pressure >180 mmHg), once daily by means of a stomach tube. The blood pressure is measured in each case 6 and, if necessary, 2 or 24 hours after administration of the substance.

The blood pressure measurement is carried out in a heated chamber at 36° C. in order to achieve better flow through the caudal artery. For this purpose, the animals are placed in perforated metal cages and measurements are carried out 20-40 min after the beginning of heating. To measure the systolic arterial pressure, an annula collar with an inflatable rubber membrane for suppressing blood flow and an annula piezocrystalline pick-up for detecting the pulse waves are pushed onto the tail. After the blood flow in the caudal artery has been suppressed, the collar pressure is reduced continuously. The return of the pulse waves when the pressure is let down is detected automatically as systolic blood pressure and is printed out (Bühler, R. et. al.: Microprocessor-based automation of blood pressure measurement in the conscious rat. Proceedings of the 4th international symposium on rats with spontaneous hypertension and related studies, Rascher, R. et al. (Eds.), Schattauer Verlag, Stuttgart, New York, 1982, pages 410–413). The pulse signals and pressure curve are plotted graphically for evaluation.

To condition them to the measuring process, the animals are trained for 14 days before testing of the substance. In the second week of training, preliminary blood pressure values are measured. Groups of animals which receive the substance are tested against a control group. In the Table below, the compounds investigated are denoted by serial numbers which correspond to the particular example numbers.

Table I shows the percentage lowering of blood pressure (BP) after oral administration in the rat for typical compounds according to the invention.

TABLE I

% changes (BP) in genetically hypertensive rats after a single daily oral administration on four successive days (N = 6/dose).

| Example No. | Dose μmol/kg | BP (change vs. control), mean value for measuring times: hours after administration (days) | | |
|---|---|---|---|---|
| | | 2h (1st + 4th day) | 6h (1st − 4th day) | 24h (1st + 3rd day) |
| 1 | 25 | −36 | −26 | 0 |
| 3 | 3 | −13 | −13 | −2 |

We claim:

1. A pure dihydropyridine enantiomer of formula I

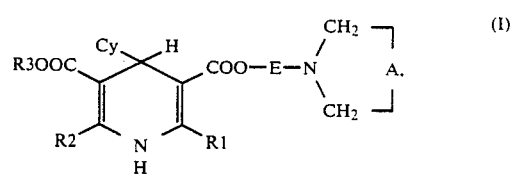

wherein Cy represents a cyclic radical of the formula

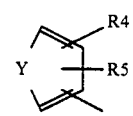

in which Y denotes oxygen (O), sulphur (S), vinylene (—CH=CH—), azomethine (—CH=N—) or a group of the formula

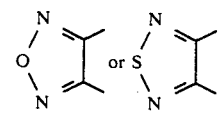

R1 and R2 are identical or different and denote hydrogen, 1-6C-alkyl or 3-7C-alkoxyalkyl, R3 denotes 1-6C-alkyl or 3-7C-alkoxyalkyl, R4 and R5 are identical or different and denote hydrogen, hydroxyl, halogen, nitro, cyano, trifluoromethyl, 1-4C-alkyl, 1-4C-alkoxy, completely or partially fluorine-substituted 1-4C-alkoxy, 1-4C-alkoxycarbonyl or 2-5C-acyl or together denote methylenedioxy, or denote amino or mono- or di-1-4C-alkylamino, E denotes straight-chain or branched 2-5C-alkylene which may be substituted by 1-4C-alkoxy or aryl, A denotes —CH₂—C(R6)R7—CH₂— or —CH₂-NR8—CH₂—, R6 denotes hydrogen (H) or aryl and R7 denotes aryl or arylcarbonyl R8 denotes aryl, aryl-1-4-C-alkyl, aryl-2-4C-alkenyl, aryl-2-4C-alkynyl, diaryl-1-4C-alkyl, heteroaryl, heteroaryl-1-4C-alkyl, heteroaryl-aryl-1-4C-alkyl, diheteroaryl-1-4C-alkyl, arylcarbonyl, heteroarylcarbonyl, arylsulphonyl, aryl1-4C-alkylcarbonyl or aryl-2-4C-alkenylcarbonyl, aryl representing a ring of the formula

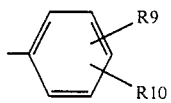

wherein R9 and R10 are identical or different and have the meaning of hydrogen (H), 1–4C-alkyl, 1–4C-alkoxy, halogen, hydroxyl or trifluoromethyl, and heteroaryl represents a 5-membered or 6-membered heterocylic radical having one heteroatom or two identical or different heteroatoms from the group consisting of oxygen (O), sulphur (S) or nitrogen (N), which is unsaturated or partially or completely saturated and which may carry one or two substituents from the group consisting of 1–4C-alkyl, 1–4C-alkoxy, halogen, trifluoromethyl or cyano, and the salts of these compounds, except for the (S)-enantiomer of the compound in which Cy has the meaning of 3-nitrophenyl, R1, R2 and R3 denote methyl, E denotes propylene, A represents $CH_2$—$C(R6)R7$—$CH_2$ and R6 and R7 denote phenyl.

2. A pure enantiomeric compound of formula I according to claim 1, wherein
Cy denotes 3-nitrophenyl or 2,3-dichlorophenyl,
R1 and R2 are identical or different and denote 1–4C-alkyl,
R3 denotes 1–4C-alkyl,
E denotes ethylene or propylene,
A denotes —$CH_2$—$C(R6)R7$—$CH_2$— or —$CH_2$—$NR8$—$CH_2$—,
R6 denotes hydrogen (H) or phenyl,
R7 denotes phenyl and
R8 denotes aryl or benzhydryl, aryl representing a ring of the formula

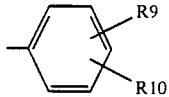

wherein R9 and R10 are identical or different and denote hydrogen (H), 1–4C-alkoxy or halogen, and the salts of these compounds, except for the (S)-enantiomer of the compound in which Cy denotes 3-nitrophenyl, R1, R2 and R3 denote methyl, E denotes propylene, A represents $CH_2$—$C(R6)R7$—$CH_2$ and R6 and R7 denote phenyl.

3. A pure enantiomeric compound of claim 1 of formula Ia

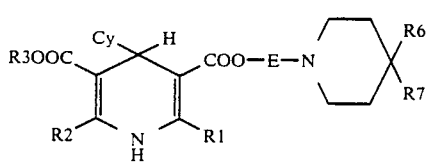

wherein
Cy denotes 3-nitrophenyl, 2-chlorophenyl, 2,3-dichlorophenyl, 2-trifluoromethylphenyl, 2-difluoromethoxyphenyl, 2,3-methylenedioxyphenyl or benzoxdiazolyl,
R1 denotes methyl or ethyl,
R2 denotes methyl or ethyl,
R3 denotes methyl or ethyl,
E denotes ethylene or propylene,
R6 denotes hydrogen and
R7 denotes phenyl, benzoyl, 4-chlorobenzoyl or 4-fluorobenzoyl, and their salts.

4. A pure enantiomeric compound of claim 1 of formula Ib

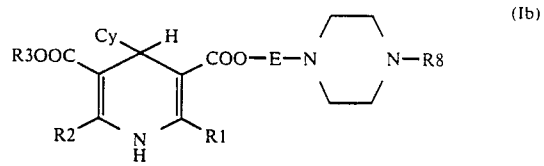

wherein
Cy denotes 3-nitrophenyl, 2-chlorophenyl, 2,3-dichlorophenyl, 2-trifluoromethylphenyl, 2-difluoromethoxyphenyl, 2,3-methylenedioxyphenyl or benzoxdiazolyl,
R1 denotes methyl or ethyl,
R2 denotes methyl or ethyl,
R3 denotes methyl or ethyl,
E denotes ethylene or propylene and
R8 denotes phenyl 2-methoxyphenyl, 2-ethoxyphenyl, 2-ethoxy-4-fluorophenyl, 3-trifluoromethylphenyl, 3-methoxyphenyl, 3,4-methylenedioxyphenyl, 2-methylphenyl, 2,4-dimethylphenyl. 2,6-dimethylphenyl, 2-pyridyl or benzhydryl, and their salts.

5. A pure enantomeric compound of claim 1 of formula Ic

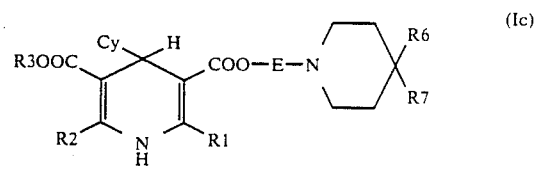

wherein
Cy denotes 3-nitrophenyl, 2-chlorophenyl, 2,3-dichlorophenyl, 2-trifluoromethylphenyl, 2-difluoromethoxyphenyl, 2,3-methylenedioxyphenyl or benzoxdiazolyl,
R1 denotes methyl or ethyl,
R2 denotes methyl or ethyl,
R3 denotes methyl or ethyl,
E denotes ethylene or propylene,
R6 denotes phenyl or 4-methoxyphenyl and
R7 denotes phenyl or 4-methoxyphenyl,
and their salts, except for the (S)-enantiomer of the compound in which Cy denotes 3-nitrophenyl, R1, R2 and R3 denote methyl, E denotes propylene and R6 and R7 denote phenyl.

6. A process for the preparation of pure enantiomeric compounds of the formula I

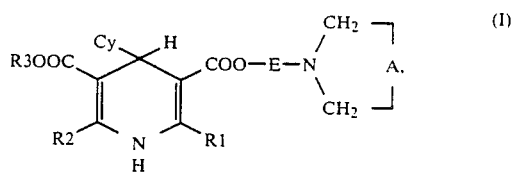

wherein Cy represents a cyclic radical of the formula

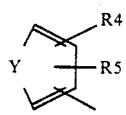

in which Y denotes oxygen (O), sulphur (S), vinylene (—CH=CH—), azomethine (—CH=N—) or a group of the formula

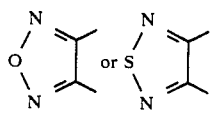

R1 and R2 are identical or different and denote hydrogen, 1-6C-alkyl or 3-7C-alkoxyalkyl, R3 denotes 1-6C-alkyl or 3-7C-alkoxyalkyl, R4 and R5 are identical or different and denote hydrogen, hydroxyl, halogen, nitro, cyano, trifluoromethyl, 1-4C-alkyl, 1-4C-alkoxy, completely or partially fluorine-substituted 1-4C-alkoxy, 1-4C-alkoxycarbonyl or 2-5C-acyl or together denote methylenedioxy, or denote amino or mono- or di-1-4C-alkylamino, E denotes straight-chain or branched 2-5C-alkylene which may be substituted by 1-4C-alkoxy or aryl, A denotes —CH$_2$—C(R6)R7—CH$_2$— or —CH$_2$—NR8—CH$_2$—, R6 denotes hydrogen (H) or aryl and R7 denotes aryl or arylcarbonyl, R8 denotes aryl, aryl-1-4C-alkyl, aryl-2-4C-alkenyl, aryl-2-4C-alkynyl, diaryl-1-4C-alkyl, heteroaryl, heteroaryl-1-4C-alkyl, heteroaryl-aryl-1-4C-alkyl, diheteroaryl-1-4C-alkyl, arylcarbonyl, heteroarylcarbonyl, arylsulphonyl, aryl-1-4C-alkylcarbonyl or aryl-2-4C-alkenylcarbonyl, aryl representing a ring of the formula

wherein R9 and R10 are identical or different and have the meaning of hydrogen (H), 1-4C-alkyl, 1-4C-alkoxy, halogen, hydroxyl or trifluoromethyl, and heteroaryl represents a 5-membered or 6-membered heterocylic radical having one heteroatom or two identical or different heteroatoms from the group consisting of oxygen (O), sulphur (S) or nitrogen (N). which is unsaturated or partially or completely saturated and which may carry one or two substituents from the group consisting of 1-4C-alkyl, 1-4C-alkoxy, halogen, trifluoromethyl or cyano, and their salts, characterised in that pure enantiomeric N-protected dihydropyridinecarboxylic acids of the formula II

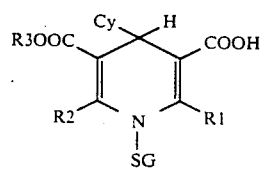

wherein R1, R2, R3 and Cy have the above-mentioned meanings and SG represents a protective group, are reacted with an omega-dihaloalkane Hal-E-Hal, wherein Hal denotes halogen and E has the above-mentioned meaning, and, after elimination of the protective group SG, the resulting haloalkyl ether III

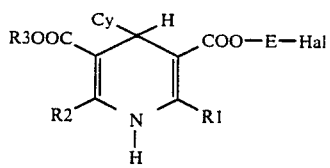

is reacted with an amine of the formula IV or a salt thereof

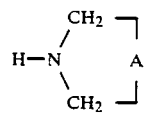

wherein A has the above-mentioned meaning, and, if desired, salts of the compound I which are obtained are then converted into the free bases or the compounds I are converted into their salts.

7. Process according to claim 6 for the preparation of 3-methyl 5-[3-(4,4-diphenylpiperid-1-yl)-propyl] (+)-1,4-dihydro-2,6-dimethyl-4-(3-nitrophenyl)-pyridine-3,5-dicarboxylate of the formula I* and its salts

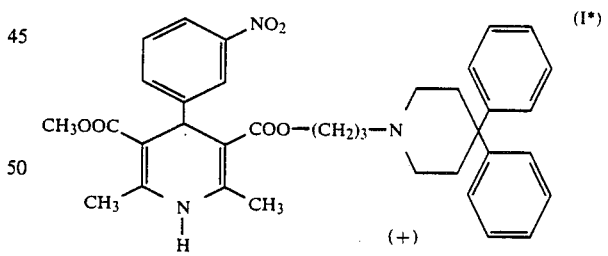

characterised in that an N-protected dihydropyridinecarboxylic acid of the formula II*

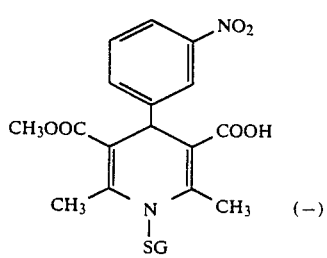

is reacted with 1,3-dibromopropane and, after elimination of the protective group SG, the resulting bromopropyl ester III*

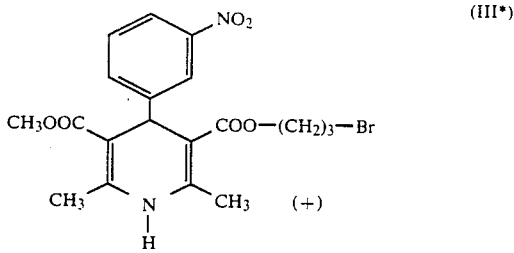

is reacted with diphenylpiperidine or a salt thereof and, if desired, a resulting salt of the compound I* is then converted into the free base or the compound I* is converted into a salt.

8. Process according to claim 6, characterized in that the protective group SG is an alkoxymethyl group or benzyloxymethyl group.

9. A medicament composition useful for treating and-/or prophylaxis of hypertension, coronary heart diseases, peripheral and cerebral circulation disorders, disorders due to increased water retention and disorders due to increased sodium retention and which comprises an effective amount of an enantiomer of claim 1 or of a pharmacologically-acceptable salt thereof in combination with suitable auxiliary or excipient.

10. A medicament composition useful for treatment and/or prophylaxis of hypertension, coronary heart diseases, peripheral and cerebral circulation disorders, disorders due to increased water retention and disorders due to increased sodium retention and which comprises an effective amount of a compound of claim 2 or of a pharmacologically-acceptable salt thereof in combination with suitable auxiliary or excipient.

11. A medicament composition useful for treatment and/or prophylaxis of hypertension, coronary heart diseases, peripheral and cerebral circulation disorders, disorders due to increased water retention and disorders due to increased sodium retention and which comprises an effective amount of a compound of claim 3 or of a pharmacologically-acceptable salt thereof in combination with suitable auxiliary or excipient.

12. A medicament composition useful for treatment and/or prophylaxis of hypertension, coronary heart diseases, peripheral and cerebral circulation disorders, disorders due to increased water retention and disorders due to increased sodium retention and which comprises an effective amount of a compound of claim 4 or of a pharmacologically-acceptable salt thereof in combination with suitable auxiliary or excipient.

13. A medicament composition useful for treatment and/or prophylaxis of hypertension, coronary heart diseases, peripheral and cerebral circulation disorders, disorders due to increased water retention and disorders due to increased sodium retention and which comprises an effective amount of a compound of claim 5 or of a pharmacologically-acceptable salt thereof in combination with suitable auxiliary or excipient.

14. A method for treatment and/or prophylaxis of hypertension, coronary heart diseases, peripheral and cerebral circulation disorders, disorders due to increased water retention and disorders due to increased sodium retention which comprises administering an effective amount of an enantiomer of claim 1 or of a pharmacologically-acceptable salt thereof to a mammal subject to or afflicted with one of the preceding conditions.

15. A method for treatment and/or prophylaxis of hypertension, coronary heart diseases, peripheral and cerebral circulation disorders, disorders due to increased water retention and disorders due to increased sodium retention which comprises administering an effective amount of a compound of claim 2 or of a pharmacologically-acceptable salt thereof to a mammal subject to or afflicted with one of the preceding conditions.

16. A method for treatment and/or prophylaxis of hypertension, coronary heart diseases, peripheral and cerebral circulation disorders, disorders due to increased water retention and disorders due to increased sodium retention which comprises administering an effective amount of a compound of claim 3 or of a pharmacologically-acceptable salt thereof to a mammal subject to or afflicted with one of the preceding conditions.

17. A method for treatment and/or prophylaxis of hypertension, coronary heart diseases, peripheral and cerebral circulation disorders, disorders due to increased water retention and disorders due to increased sodium retention which comprises administering an effective amount of a compound of claim 4 or of a pharmacologically-acceptable salt thereof to a mammal subject to or afflicted with one of the preceding conditions.

18. A method for treatment and/or prophylaxis of hypertension, coronary heart diseases, peripheral and cerebral circulation disorders, disorders due to increased water retention and disorders due to increased sodium retention which comprises administering an effective amount of a compound of claim 5 or of a pharmacologically-acceptable salt thereof to a mammal subject to or afflicted with one of the preceding conditions.

19. A pure enantiomer of claim 1 which, in the 4-position of the dihydropyridine, has the same configuration as the (+)-1-ethoxymethyl-1,4-dihydro-5-methoxycarbonyl-2,6-dimethyl-4-(3-nitrophenyl)-pyridine-3-carboxylic acid cinchonine salt which can be used as a precursor and which rotates linearly polarized light of wavelength 589 nm through $[\alpha]^{22}_D = +101.5°$ (c=1, methanol); or a salt thereof.

20. A pure enantiomer of claim 19 which is (−)-3-methyl-5-[3-(4,4-diphenyl-1-piperidinyl)-propyl]-1,4-dihydro-2,6-dimethyl-4-(3-nitrophenyl)-pyridine-3,5-dicarboxylate or a pharmacologically-acceptable salt thereof.

21. An antiarteriosclerotic composition comprising an effective amount of a compound of claim 19 or of a pharmacologically-acceptable salt thereof and a pharmacologically-acceptable carrier.

22. A method for treatment and/or prophylaxis of arteriosclerosis which comprises administering an effective amount of an enantiomer of claim 19 or of a pharmacologically-acceptable salt thereof to a mammal subject to or afflicted with arteriosclerosis.

* * * * *

UNITED STATES PATENT AND TRADEMARK OFFICE
CERTIFICATE OF CORRECTION

PATENT NO. : USP 4,994,461  
DATED : February 19, 1991  
INVENTOR(S) : ULRICH

Page 1 of 2

It is certified that error appears in the above-identified patent and that said Letters Patent is hereby corrected as shown below:

Column 1, line 6, "processes" should read --, processes--.
Column 2, line 55, "tert-butyl" should read --tert-butyl,--;
line 56, "particular" should read --particular,--; line 65, "contains" should read --contains,--.  Column 3, line 1, "contains" should read --contains,--; line 4, "contains" should read --contains,--; line 27, "2.5-" should read --2,5- --; line 55, "particular" should read --particular,--; line 58, "dimethoxyhydryl" should read --dimethoxybenzhydryl--.  Column 4, line 16, "solvents" should read --salts--; line 19, "citrate" should read --citrate,--; line 20, "sulphosalicylate" should read --sulphosalicylate,--; line 23, "naphtoate" should read --naphthoate--; line 62, "-CH-" should read -- -CH$_2$- --.  Column 7, line 63, "5-(2" should read --5-{2--.  Column 8, line 1, "3-methyl5" should read --3-methyl 5--; line 25, "methylenedixoyphenyl" should read --methylenedioxyphenyl--; line 28, "methylenedixoyphenyl" should read --methylenedioxyphenyl--; line 54, "2,3-chloro-" should read --2,3-dichloro- --.  Column 9, line 63, "methylenedixoyphenyl" should read --methylenedioxyphenyl--.  Column 11, line 32, "3-methyl5" should read --3-methyl 5--; line 54, "2.3" should read --2,3--.  Column 12, line 22, "or" should read --(-CH=N-) or--; line 50, "aryl-2 4C" should read --aryl-2-4C--.  Column 14, line 28, "esters lll" should read --esters III--; line 32, "preferably inert" should read --, preferably inert, --; line 37, "ketone" should read --ketone;--; line 39, "chloride" should read --chloride,--; line 41, "vents" should read --vents,--.  Column 17, line 40, "exchange" should read --exchange,--; line 48, "23" should read --23--; line 60, each of "EXAMPLES" and "End Products" should be on separate lines.  Column 18, line 50, "5-3" should read --5-[3--; line 54, "1.3 8" should read --1.3 g--.  Column 20, line 39, "+)" should read --(+)--.  Column 21,

UNITED STATES PATENT AND TRADEMARK OFFICE
CERTIFICATE OF CORRECTION

Page 2 of 2

PATENT NO. : USP 4,994,461
DATED : February 19, 1991
INVENTOR(S) : ULRICH

It is certified that error appears in the above-identified patent and that said Letters Patent is hereby corrected as shown below:

line 15, "dihdyrochloride" should read --dihydrochloride--; line 16, "6." should read --6,--; line 21, "2,6" should read --2.6--; line 25, "STARTING COMPOUNDS" should be on a separate line; line 26, "bromopropyl)" should read --bromopropyl)--; line 60, "8" should read --B--. Column 22, line 16, "vacuo" should read --vacuo,--; line 23, "2" should read --2,--. Column 23, line 27, "(±(" should read --(±)--. Column 24, line 38, "ml" should read --30 ml--; line 62, "water." should read --water,--. Column 25, line 46, "temperature." should read --temperature,--. Column 28, line 10, "effect" should read --effective--. Column 29, line 9, "dihydralazine" should read --dihydralazine,--. Column 30, line 5, "change" should read --% change--; line 65, "aryll" should read --aryl-1--. Column 32, line 26, "phenyl" should read --phenyl,--. Column 35, line 24 (Claim 9, line 1), "treating" should read --treatment--.

Signed and Sealed this

Twenty-fourth Day of November, 1992

Attest:

DOUGLAS B. COMER

Attesting Officer

Acting Commissioner of Patents and Trademarks